US005712094A

United States Patent [19]
Seidel et al.

[11] Patent Number: 5,712,094
[45] Date of Patent: Jan. 27, 1998

[54] METHODS FOR DETECTING MODULATORS OF CYTOKINE ACTION

[75] Inventors: H. Martin Seidel; I. Peter Lamb; Shin-Shay Tian Chan, all of San Diego, Calif.

[73] Assignee: Ligand Pharmaceuticals, Inc., San Diego, Calif.

[21] Appl. No.: 411,020

[22] Filed: Mar. 27, 1995

[51] Int. Cl.$^6$ .................................................. C12Q 1/68
[52] U.S. Cl. .................... 435/6; 536/23.1; 435/252.3; 435/325; 435/320.1; 935/33; 935/34; 935/36; 935/70
[58] Field of Search .................. 435/6, 240.2, 252.3, 435/320.1, 325; 536/23.1; 935/33, 34, 36, 70

[56] References Cited

FOREIGN PATENT DOCUMENTS

| | | |
|---|---|---|
| 487298A2 | 11/1991 | European Pat. Off. |
| 692488A2 | 1/1996 | European Pat. Off. |
| WO9213091 | 8/1992 | WIPO |
| 9508001 | 3/1995 | WIPO |
| 9528482 | 10/1995 | WIPO |
| 9528492 | 10/1995 | WIPO |

OTHER PUBLICATIONS

Peterson et al. (1993) Trends in Biotech vol. 11. pp. 11–18.
Seidel, H., Milocco, L., Lamb, P.,Darnell, J. Jr., Stein, R., and Rosen, J., "Spacing of palindromic half sites as a determinant of selective STAT (signal transducers and activators of transcription) DNA binding and transcriptional activity," *Proceedings of the National Academy of Sciences of the United States*, vol. 92, No. 7, pp. 3041–3045, (1995).
Kotanides, H., and Reich, N., "Requirement of Tyrosine Phosphorylation for Rapid Activation of a DNA Binding Factor by IL–4," *Science*, vol. 262, pp. 1265–1267 (1993).
Ihle, J., Witthuhn, B., Quelle, F., Yamamoto, K., Thierfelder, W., Kreider, B., and Silvennoinen, O., "Signaling by the cytokine receptor superfamily: JAKs and STATs," *TIG*, pp. 222–227 (1994).
Schindler, C., Kashleva, H., Pernis, A., Pine, R., and Rothman, P., "STF–IL–4: a novel IL–4–induced signal transducing factor," *The EMBO Journal*, vol. 13, No. 6, pp. 1350–1356 (1994).
Ihle, J. and Kerr, L, "Jaks and Stats in signaling by the cytokine receptor superfamily," *TIG*,vol. 11, No. 2, pp. 69–74 (1995).
Lamb, P., Seidel, H., Haslam, J., Milocco, L., Kessler, L., Stein, R., and Rosen, J., "STAT protein complexes activated by interferon–γ and gp130 signaling molecules differ in their sequence preferences and transcriptional induction properties," *Nucleic Acids Research*, vol. 23, No. 16, pp. 3283–3289 (1995).
International Search Report, US96/04012, concurrent PCT application to Applicants' Docket No. 016–0030.US.

Lew, D.; Decker, T.; Strehlow, I.; and Darnell, J., "Overlapping Elements in the Guanylate–Binding Protein Gene Promoter Mediate Transcriptional Induction by Alpha and Gamma Interferons," *Molecular and Cellular Biology*, vol. II, No. 01, pp. 182–191 (1991).
Decker, T.; Lew, D.; and Darnell, J., "Two Distinct Alpha–Interferon–Dependent Signal Transduction Pathways May Contribute to Activation of Transcription of the Guanylate–Binding Protein Gene," *Molecular and Cellular Biology*, vol. II, No. 10, pp. 5147–5153 (1991).
Decker, T.; Lew, D.; Mirkovitch, J.; and Darnell, J., "Cytoplasmic activation of GAF, an IFN–γ–regulated DNA–binding factor," *The EMBO Journal*, vol. 10, No. 4, pp. 927–932 (1991).
Akira, S.; Nishio, Y.; Inoue, M.; Wang, X.; Wei, S.; Matsusaka, T.; Yoshida, K.; Sudo, T.; Naruto, M.; and Kishimoto, T., "Molecular Cloning of APRF, a Novel IFN––Stimulated Gene Factor 3 p91–Related Transcription Factor Involved in the gp 130–Mediated Signaling Pathway," *Cell*,vol. 77, pp. 63–71 (1994).
Hattori, M.; Abraham, L.; Northemann, W.; and Fey, G., "Acute–phase reaction induces a specific complex between hepatic nuclear proteins and the interleukin 6 response element of the rat $\alpha_2$–macroglobulin gene," *Proc. Natl. Acad. Sci. USA*, vol. 87, pp. 2364–2368 (1990).
Wegenka, U.; Buschmann, J.;Lütticken, C.; Heinrich, P., and Horn, F., "Acute–Phase Response Factor, a Nuclear Factor Binding to Acute–Phase Response Elements, is Rapidly Activated by Interleukin–6 at the Posttranslational Level," *Molecular and Cellular Biology*, vol. 13, No. 1, pp. 276–288 (1993).
Ito, T.; Tanahashi H.; Misumi, Y.; and Sakaki,Y., "Nuclear factors interacting with an interleukin–6 responsive element of a rat $\alpha_2$–macroglobulin gene," *Nucleic Acids Research*, vol. 17, No. 22, pp. 9425–9435 (1989).
Hocke, G.; Barry, D.; and Fey, G., "Synergistic Action of Interleukin–6 and Glucocorticoids Is Mediated by the Interleukin–6 Response Element of the Rat $\alpha_2$–Macroglobulin Gene," *Molecular and Cellular Biology*, vol. 12, No. 5, pp. 2282–2294 (1992).

(List continued on next page.)

*Primary Examiner*—John Ulm
*Assistant Examiner*—Prema Mertz
*Attorney, Agent, or Firm*—J. Scott Elmer

[57] ABSTRACT

The present invention provides DNA constructs that contain oligonucleotide sequences comprising DNA regulatory elements of the general sequence TTN$_x$AA that bind activated transcriptional regulatory proteins in response to signaling molecules, such as cytokines, an operably linked promoter and operably linked heterologous gene. The present invention also provides host cells transfected with such DNA constructs, as well as methods for measuring the ability of compounds to act as agonists and antagonists of gene transcription utilizing these DNA constructs and transfected host cells.

4 Claims, 1 Drawing Sheet

OTHER PUBLICATIONS

Yuan, J.; Wegenka, U.; Lütticken, C.; Buschmann, J.; Decker, T.; Schindler, C.; Heinrich, P.; and Horn, F., "The Signalling Pathways of Interleukin–6 and Gamma Interferon Converge by the Activation of Different Transcription Factors Which Bind to Common Responsive DNA Elements," *Molecular and Cellular Biology*, vol. 14, No. 3, pp. 1657–1668 (1994).

Kunz D.; Zimmermann, R.; Heisig, M.; and Heinrich, P., "Identification of the promoter sequences involved in the interleukin–6 dependent expression of the rat $\alpha_2$–macroglobulin gene," *Nucleic Acids Research*, vol. 17, No. 3, pp. 1121–1138 (1989).

Khan, K.; Lindwall, G.; Maher, S.; and Bothwell, A., "Characterization of Promoter Elements of an Interferon–Inducible Ly–6E/A Differentiation Antigen, Which Is Expressed on Activated T Cells and Hematopoietic Stem Cells," *Molecular and Cellular Biology*, vol. 10, No. 10, pp. 5150–5159 (1990).

Khan, K.; Shuai, K.; Lindwall, G.; Maher, S.; Darnell, J.; and Bothwell, A., "Induction of the Ly–6A/E gene by interferon $\alpha/\beta$ and $\gamma$ requires a DNA element to which a tyrosine–phosphorylated 91–kDa protein binds," *Proc. Natl. Acad. Sci. USA*, vol. 90, pp. 6806–6810 (1993).

Sadowski, H. and Gilman, M., "Cell–free activation of a DNA–binding protein by epidermal growth factor," *Nature*, vol. 362, pp. 79–83 (1993).

Wagner, B.; Hayes, T.; Hoban, C.; and Cochran, B., "The SIF binding element confers sis/PDGF inducibility onto the c–fos promoter," *The EMBO Journal*, vol. 9, No. 13, pp. 4477–4484 (1990).

Strehlow, I. and Decker, T., "Transcriptional induction of IFN–$\gamma$–responsive genes is modulated by DNA surrounding the interferon stimulation response element," *Nucleic Acids Research*, vol. 20, No. 15, pp. 3865–3872 (1992).

Wong, P.; Severns, C.; Guyer, N.; and Wright, T., "A Unique Palindromic Element Mediates Gamma Interferon Induction of mig Gene Expression," *Molecular and Cellular Biology*, vol. 14, No. 2, pp. 914–922 (1994).

Silvennoinen, O.; Schindler, C.; Schlessinger, J.; and Levy, D., "Ras–independent Growth Factor Signaling by Transcription Factor Tyrosine Phosphorylation," *Science*, vol. 261, pp. 1736–1739 (1993).

Ruff–Jamison, S.; Chen, K.; and Cohen, S., "Induction by EGF and Interferon–$\gamma$ of Tyrosine Phosphorylated DNA Binding Proteins in Mouse Liver Nuclei," *Science*, vol. 261, pp. 1733–1736 (1993).

Larner, A.; David, M.; Feldman, G.; Igarashi, K.; Hackett, R.; Webb, D.; Sweitzer, S.; Petricoin, E.; and Finbloom, D., "Tyrosine Phosphorylation of DNA Binding Proteins by Multiple Cytokines," *Science*, vol. 261, pp. 1730–1733 (1993).

Shuai, K.; Stark, G.; Kerr, I.; and Darnell, J., "A Single Phosphotyrosine Residue of Stat91 Required for Gene Activation by Interferon–$\gamma$," *Science*, vol. 261, pp. 1744–1746 (1993).

Sadowski, H.; Shuai, K.; Darnell, J.; and Gilman, M., "A Common Nuclear Signal Transduction Pathway Activated by Growth Factor and Cytokine Receptors," *Science*, vol. 261, pp. 1739–1744 (1993).

Kanno, Yuka; Kozak, C.; Schinlder, C.; Driggers, P.; Ennist, D.; Gleason, S.; Darnell, J.; and Ozato, K., "The Genomic Structure of the Murine ICSBP Gene Reveals the Presence of the Gamma Interferon–Responsive Element, to Which an ISGF3$\alpha$ Subunit (or Similar) Molecule Binds," *Molecular and Cellular Biology*, vol. 13, No. 7, pp. 3951–3963 (1993).

Harroch, S.; Revel, M.; and Chebath, J., "Induction by interleukin–6 of interferon regulatory factor 1 (IRF–1) gene expression through the palindromic interferon response element pIRE and cell type–dependent control of IRF–1 binding to DNA," *The EMBO Journal*, vol. 13, No. 8, pp. 1942–1949 (1994).

Sims, S.; Cha, Y.; Romine, M.; Gao, P.; Gottlieb, K.; and Deisseroth, A., "A Novel Interferon–Inducible Domain: Structural and Functional Analysis of the Human Interferon Regulatory Factor 1 Gene Promoter," *Molecular and Cellular Biology*, vol. 13, No. 1, pp. 690–702 (1993).

Pearse, R.; Feinman, R.; Shuai, K.; Darnell, J.; and Ravetch, J., "Interferon $\gamma$–induced transcription of the high–affinity Fc receptor for IgG requires assembly of a complex that includes the 91–kDa subunit of transcription factor ISGF3," *Proc. Natl. Acad. Sci. USA*, vol. 90, pp. 4314–4318 (1993).

Pearse, R.; Feinman, R.; and Ravetch, J., "Characterization of the promoter of the human gene encoding the high affinity IgG receptor: Transcriptional induction by $\gamma$–interferon is mediated through common DNA response elements," *Proc. Natl. Acad. Sci. USA*, vol. 88, pp. 11305–11309 (1991).

Kotanides, H. and Reich, N., "Requirement of Tyrosine Phosphorylation for Rapid Activation of a DNA Binding Factor by IL–4," *Science*, vol. 262, pp. 1265–1267 (1993).

Schindler, C.; Kashleva H.; Pernis, A.; Pine, R.; and Rothman, P., "STF–IL–4: a novel IL–4–induced signal transducing factor," *The EMBO Journal*, vol. 13, No. 6, pp. 1350–1356 (1994).

Li, P.; He, X.; Gerrero, M.; Mok, M.; Aggarwal, A.; and Rosenfeld, M., "Spacing and orientation of bipartite DNA–binding motifs as potential functional determinants for POU domain factors," *Genes & Development*, vol 7, pp. 2483–2496 (1993).

Carlberg, C., "RXR–Independent Action of the Receptors for Thyroid Hormone, Retinoid Acid and Vitamin D on Inverted Palindromes," *Biochemical and Biophysical Research Communications*, vol. 195, No. 3, pp. 1345–1353 (1993).

Mangelsdorf, D., et al., "Retinoid Receptors," *The Retinoids: Biology, Chemistry and Medicine*, 2nd ed., pp. 331–332 (1994).

Umesono, K.; Murakami, K.; Thompson, C.; and Evans, R., "Direct Repeats as Selective Response Elements for the Thyroid Hormone, Retinoic Acid, and Vitamin $D_3$ Receptors," Cell. vol. 65, pp. 1255–1266 (1991).

Näär, A.; Boutin, J.; Lipkin, S.; Yu, V.; Holloway, J.; Glass, C.; and Rosenfeld, M., "The Orientation and Spacing of Core DNA–Binding Motifs Dictate Selective Transcriptional Responses to Three Nuclear Receptors," *Cell*, vol. 65, pp. 1267–1279 (1991).

Reid, L.; Brasnett, A.; Gilbert, C.; Porter, A.; Gewert, D.; Stark, G.; and Kerr, I., "A single DNA response element can confer inducibility by both $\alpha$–and $\gamma$–interferons," *Proc. Natl. Acad. Sci. USA*, vol. 86, pp. 840–844 (1989).

Wakao, H., Gouilleux, F., and Groner, B., "Mammary gland factor (MGF) is a novel member of the cytokine regulated transcription factor gene family and confers the prolactin response," *The EMBO Journal*, vol. 13, No. 9, pp. 2182–2191 (1994).

Mui, A., Wakao, H., O'Farrell, A., Harada, N., and Miyajima, A., "Interleukin-3, granulocyte-macrophage colony stimulating factor and interleukin-5 transduce signals through two STAT5 homologs," *The EMBO Journal*, vol. 14, No. 6, pp. 1166–1174 (1995).

Drachman, J., Griffin, J., and Kaushansky, K., "The c-Mp1 Ligand (Thrombopoietin) Stimulates Tyrosine Phosphorylation of Jak2, Shc, and c-Mp1," *The Journal of Biological Chemistry*, vol. 270, No. 10, pp. 4979–4982 (1995).

Beading, C., Gushin, D., Witthuhn, B., Ziemiecki, A., Ihle, J., Kerr, I., and Cantrell, D., "Activation of JAK kinases and STAT proteins by interleukin-2 and interferon α, but not the T cell antigen receptor, in human T lymphocytes," *The EMBO Journal*, vol. 13, No. 23, pp. 5605–5615 (1994).

Gouilleux, F., Wakao, H., Mundt, M., and Groner, B., "Prolactin induces phosphorylation of Tyr694 of Stat5 (MGF), a prerequisite for DNA binding and induction of transcription," *The EMBO Journal*, vol. 13, No. 18, pp. 4361–4369 (1994).

Standke, G., Meier, V., and Groner, B., "Mammary Gladn Factor Activated by Prolactin in Mammary Epithelial Cells and Acute-Phase Response Factor Activated by Interleukin-6 in Liver Cells Share DNA Binding and Transactivation Potential," *Molecular Endocrinology*, vol. 8, No. 4, pp. 469–477 (1994).

Delphin, S., and Stavnezer, J., "Characterization of an Interleukin 4 (IL-4) Responsive Region in the Immunoglobulin Heavy Chain Germline ε Promoter: Regulation by NF-IL-4, a C/EBP Family Member and NK-κB/p50," *J. Exp. Med.*, vol. 181, pp. 181–192 (1995).

Albrechet, ., Peiritsch, S., and Woisetschläger, M., "A bifunctional control element in the human lgE germline promoter involved in repression and IL-4 activation," *International Immunology*, vol. 6, No. 8, pp. 1143–1151 (1994).

Coffer, P., Lutticken, C., Puijenbroek, A., Jonge, M., Horn, F., and Kruijer, W., "Transcriptional regulation of the junB promoter: analysis of STAT-mediated signal transduction," *Oncogene*, vol. 10(5) pp. 985–994 (1995).

Fujitani, Y., Nakajima, K., Kojima, H., Nakae, K., Takeda, ., and Hirano,T., "Transcriptional Activation of the IL-6 Response Element in the JunB Promoter is Mediated by Multiple STAT Family Proteins," *Biochemical and Biophysical Research Communications*, vol. 202, No. 2, pp. 1181–1187 (1994).

Hou, J., Schindler, U., Henzel, W., Ho, T., Brasseur, M., and McKnight, S., "An Interleukin-4–Induced Transcription Factor: IL-4 STAT," *Science*, vol. 265, pp. 1701–1706 (1994).

Rothman, P.; Kreider, B.; Azam, M.; Levy, D.; Wegenka, U.; Eilers, A.; Decker, T.; Horn, F.; Hashleva, H.; Ihle, J.; and Schindler, C., "Cytokines and Growth Factors Signal Through Tyrosine Phosphorylation of a Family of Related Transcription Factors," *Immunity*, vol. 1 pp. 457–468 (1994).

Lamb, P.; Kessler, L. V.; Suto, C.; Levy, D.E.; Seidel, H.M.; Stein, R.B.; and Rosen, J., "Rapid Activation of Proteins that Interact with the Interferon-γ Activation Site in Response to Multiple Cytokines" *Blood*, vol. 83, No. 8, pp. 2063–2071 (1994).

METHODS FOR DETECTING MODULATORS OF CYTOKINE ACTION

FIELD OF THE INVENTION

This invention relates to methods for detecting modulators of cytokine action, and to DNA constructs and transfected host cells useful in said assays.

BACKGROUND OF THE INVENTION

In many cellular systems, extracellular signaling molecules, such as polypeptide ligands, bind to receptors on the surface of the cells, thereby triggering an intracellular signaling pathway that ultimately regulates gene transcription within the cells. For example, cytokines and growth factors, which comprise a large and diverse family of soluble polypeptides that control the growth, differentiation and function of mammalian cells, bind to specific cell surface receptors, that in some way transduce signals that elicit a specific phenotypic response. A. Miyajama et al., 10 *Annu. Rev. Immunol.*, 295 (1992); M. Aguet et al., 55 *Cell*, 273 (1988); T. Kishimoto et al., 258 *Science*, 593 (1992) and A. Ullrich and J. Schlessinger, 61 *Cell*, 203 (1990). Abundant evidence shows that changes in the transcription rate of specific genes are an important component of this response. This is thought to be a consequence of alterations in the amount or the activity of specific DNA-binding proteins.

In some instances, progress has been made in defining the pathway that leads from a receptor-ligand interaction at the cell surface to changes in the activity of such DNA binding proteins or other nuclear proteins. Ullrich, 61 *Cell* 203. In this regard, a common response in surface receptor signaling pathways involves the activation of Ras. L. S. Mulcahy et al., 313 *Nature*, 24 (1985). Activated Ras then initiates a cascade of serine/threonine phosphorylations through MAP kinases leading to phosphorylation of DNA binding proteins, thereby changing their transcriptional modulatory activity. S. A. Moodie et al., 260 *Science*, 1658 (1993); C. A. Lange-Carter et al., 260 *Science*, 315 (1993); C. S. Hill et al., 73 *Cell* 395 (1993); H. Gille et al., 358 *Nature*, 414 (1992) and R. H. Chen et al., 12 *Mol. Cell. Biol.*, 915 (1992).

Despite these advances, the signal transduction pathways utilized by many growth factors and cytokines to alter gene expression remain unclear. Thus, although known second messengers have been implicated in signal transduction in response to some of these factors, their role in modulating gene expression remains speculative. Miyajama, 10 *Annu. Rev. Immunol.*, 295 and D. E. Levy and J. E. Darnell, 2 *New Biol.*, 923 (1990). This in turn raises the question of how ligand specific responses are elicited in such cellular systems. Ullrich, 61 *Cell*, 203; M. V. Chao, 68 *Cell*, 995 (1992) and Levy, 2 *New Biol.*, 923.

Progress in resolving these issues has been made recently in the interferon (IFN) system. IFNs α and β (type I) act as a primary non-specific defense against viral infections. S. Petska and J. A. Langer, 56 *Annu. Rev. Biochem.*, 727 (1987). IFN$_\gamma$ (type II) has anti-viral properties but also plays a major role in regulation of the immune response. Id. Type I and type II IFNs bind to distinct cell surface receptors and cause rapid alterations in gene expression. Aguet, 55 *Cell*, 273; Uze, 60 *Cell*, 225; and G. C. Sen and P. Lengyel, 267 *J. Biol. Chem.*, 5017 (1992). Specific sequence elements have been identified in the promoters of genes that respond to IFNα, termed interferonα stimulated response elements (ISREs), that are both necessary and sufficient for regulation by IFNα. Sen, 267 *J. Biol. Chem.*, 5017. Specifically, activation of the IFNα receptors stimulates tyrosine phosphorylation of a family of proteins that serve as DNA binding proteins, and accordingly as transcription regulatory factors via the ISRE. C. Schindler et al., 257 *Science*, 809 (1992); K. Shuai et al., 258 *Science*, 1808 (1992) and M. J. Gutch et al., 89 *Proc. Natl. Acad. Sci. USA*, 11411 (1992). These DNA binding proteins, generically termed "signal transducers and activators of transcription" (STATs), assemble into a multimeric complex, translocate to the nucleus, and bind cis-acting enhancer elements in the appropriate regulatory regions. D. E. Levy et al., 3 *Genes Dev.*, 1362 (1989); and D. S. Kessler et al., 4 *Genes Dev.*, 1753 (1990) and Z. Zhong et al., 264 *Science*, 95 (1994).

One example of an IFNα-induced ISRE binding protein complex is ISGF3. T. C. Dale et al., 86 *Proc. Natl. Acad. Sci.*, 1203 (1989) and X.-Y. Fu et al., 87 *Proc. Natl. Acad. Sci.*, 8555 (1990). ISGF3 is a complex of 4 binding proteins, called p48, p84 (STAT 1β), p91 (STAT 1α) and p113 (STAT2). Recently, cDNAs encoding the proteins that constitute ISGF3 have been isolated and characterized. X.-Y. Fu et al., 89 *Proc. Natl. Acad. Sci.*, 7840 (1992); C. Schindler et al., 89 *Proc. Natl. Acad. Sci.*, 7836 (1992) and S. A. Veals et al., 12 *Mol. Cell. Biol.*, 3315 (1992). p48 is the DNA binding component of ISGF3 and has homology to myb. Veals, 12 *Mol. Cell. Biol.*, 3315. p84 and p91 are probably alternatively spliced products of the same gene and are related to p113. X.-Y. Fu, 89 *Proc. Natl. Acad. Sci.*, 7840 and Schindler, 89 *Proc. Natl. Acad. Sci.*, 7836. p84, p91 and p113 are novel proteins that contain SH2 and SH3 domains and are found in the cytoplasm of untreated cells. Schindler, 257 *Science*, 809 and X. Y. Fu, 70 *Cell*, 323–335 (1992). Thus, IFNα treatment of cells results in rapid tyrosine phosphorylation of p84, p91 and p113, causing them to associate and form a heteromeric complex with p48 to form ISGF3, which then translocates to the nucleus and binds to ISREs, stimulating transcription. Id.; Dale, 86 *Proc. Natl. Acad. Sci.*, 1203 and Kessler, 4 *Genes Dev.*, 1753.

Regulation in response to IFNγ is conferred by a distinct sequence from the ISRE, the gamma activated sequence (GAS). T. Decker et al., 10 *EMBO J.*, 927 (1991); K. D. Khan et al., 90 *Proc. Natl. Acad. Sci.*, 6806 (1993) and D. J. Lew et al., 11 *Mol. Cell. Biol.*, 182 (1991). Treatment of cells with IFNγ results in tyrosine phosphorylation of p91 (STAT1α), which then translocates to the nucleus and binds to the GAS. Decker, 10 *EMBO J*, 927 and K. Shuai et al., 258 *Science*, 1808 (1992). Thus the specificity of binding of either IFNα or IFNγ to their receptors is translated into a specific phosphorylation pattern within a related family of latent transcription factors (i.e. DNA binding proteins). This pattern of phosphorylation dictates the association state of the proteins, which determines specificity of binding to either an ISRE or a GAS, and the subsequent transcriptional response.

Yet another cytokine, Interleukin-6 (IL-6) plays a major role in the induction of the acute phase response in hepatocytes. The acute phase response is characterized by the dramatic transcriptional upregulation of a distinct set of genes, termed acute phase response genes. P. C. Heinrich et al, 265 *Biochem. J.*, 621–636 (1990). Studies of the promoter regions of these genes have identified specific DNA sequences that are required for induction of acute phase response genes by IL-6. See D. R. Kunz et al., 17 *Nuc. Acids Res.*, 1121–1138 (1989); M. Hattori et al., 87 *Proc. Natl. Acad. Sci USA*, 2364–2368 (1990); K. A. Won and H. Baumann, 10 *Mol. Cell. Biol.*, 3965–3978 (1990) and D. R. Wilson et al., 10 *Mol. Cell. Biol.*, 6181–6191 (1990). These sequences are termed acute phase response elements (APREs). One type of APRE shows many similarities to the GAS elements that confers induction by IFNγ. Yuan et al., 14 *Mol. Cell. Biol.*, 1657–1668 (1994). Proteins that bind to this class of APREs have been characterized and purified. U. M. Wegenka et al., 13 *Mol. Cell. Biol.*, 276–288 (1993); T. Ito et al., 17 *Nuc. Acids Res.*, 9425–9435 (1989) and Hattori, 87 *Proc. Natl. Acad. Sci. USA*, 2364–2368. A cDNA clone encoding the IL-6-induced APRE-binding protein has been isolated (Zhong, 264 *Science*, 95 (1994); Akira et al, 77 *Cell*, 63 (1994); Zhong et al. 91 *Proc. Natl. Acad. Sci.*, 4806 (1994) and Raz et al., 269 *J. Biol. Chem.*, 24391 (1994)), and was found to encode a protein that shows considerable homology to p91 (STAT1α). For this reason the protein is termed STAT3. Like STAT1α, STAT3 is a latent transcription factor that is activated to bind DNA by rapid tyrosine phosphorylation.

Interleukin-4 (IL-4) is a pleiotropic cytokine that elicits biological responses in a variety of both lymphoid and non-lymphoid cell types. IL-4 is a glycoprotein of approximately 19 kD produced primarily by the Th2 subset of activated T-cells. IL-4 has since been shown to play an important role in B-cell proliferation, the regulation of immunoglobulin expression, in T-cell regulation and in the growth and differentiation of hematopoietic precursor cells. IL-4 exerts its biological effects through a specific high-affinity receptor on the surface of hematopoietic as well as certain non-hematopoietic cell lines. One chain of its receptor, the $\gamma_c$ chain, is shared by the IL-2, IL-7, IL-9 and IL-13 receptors. M. Kondo et al., 262 *Science* 1874 (1993), M. Noguchi et al., 262 *Science* 1877 (1993), S. Russell et al., 262 *Science* 1880 (1993), and M. Kondo et al., 263 *Science* 1453 (1994).

Binding of IL-4 to its receptor on the cell surface results in the activation of an intracellular tyrosine kinase and the rapid phosphorylation of several proteins on tyrosine. These initial events appear to be directly related to the immediate effects of IL-4 on target gene transcription. In particular, IL-4 up-regulates in responsive cell lines the expression of several cell-surface antigens including class II MHC, the low affinity Fc receptor for IgE (FcεRII, CD23), LFA-1 and LFA-3, CD40 and surface IgM. B. Aggarwal and J. U. Gutterman, *Human Cytokines: Handbook for Basic Chemical Research* Blackwell Scientific Publications, Boston, Mass. (1992). Perhaps the most prominent role of IL-4 is in B-cell differentiation, where IL-4 acts as a "switch factor" promoting an Ig heavy chain class switch to IgE, the major mediator of Type I allergic reactions. W. E. Paul, 77 *Blood* 1859 (1991). Evidence that IL-4 operates through a STAT signal transduction system is based upon the observation that IL-4 rapidly activates in a variety of cell lines phosphotyrosine-containing protein complexes that bind to a GAS-like DNA sequence element. H. Kotanides and N. Reich 262 *Science* 1265 (1993) and C. Schindler et al., 13 *EMBO J.* 1350 (1994); P. Lamb et al., 83 *Blood*, 2063 (1994) and I. Kohler and E. P. Rieber, 23 *Eur. J. Immunol.*, 3066 (1993). A STAT activated by IL-4 in THP-1 cells has been cloned recently (called STAT-IL-4 or STAT6) and is likely a constituent of all of the reported IL-4 induced complexes. J. Hou et al., 265 *Science*, 1701 (1994) and J. N. Ihle et al., 11 *Trends in Genetics*, 69 (1995).

Interleukin 13 (IL-13) is a pleiotropic cytokine that shares many of the biological activities of IL-4. G. Zurawski and J. E. de Vries, 15 *Immunol. Today* 19 (1994). IL-13 has roughly 30% sequence identity with IL-4 and exhibits IL-4-like activities on monocytes/macrophages and B-cells (A. Minty et al., 362, *Nature* 248 (1993) and A. N. J. McKenzie et al., 90 *Proc. Natl. Acad. Sci. USA* 3735 (1993). However, unlike IL-4, IL-13 has no effect on T-cells. The biological activity of IL-13 is mediated through binding to its specific high-affinity cell surface receptors consisting of an IL-13 binding subunit and one or more receptor components that are shared with the IL-4 receptor (the 'IL-4R' subunit and/or the γc subunit). G. Aversa et al., 178 *J. Exp. Med.* 2213 (1993). Evidence that IL-13, like IL-4, operates through a STAT signal transduction system is based upon the observation that IL-13 rapidly activates in a variety of cell lines phosphotyrosine-containing protein complexes very similar to those induced by IL-4 that bind to a GAS-like DNA sequence element. I. Köhler et al., 345 *FEBS Lett.* 187 (1994).

GM-CSF belongs to a group of growth factors termed colony stimulating factors which are involved in the survival, clonal expansion, and differentiation of hematopoietic progenitor cells. J. Gasson, 77 *Blood* 1131 (1991) and N. A., Nicola, 58 *Annu Rev. Biochem.* 45 (1989). GM-CSF acts on a set of partially committed progenitor cells and causes them to divide and differentiate in the granulocytemacrophage pathways. GM-CSF can also activate mature granulocytes and macrophages. In addition to effects on myelomonocytic lineages, GM-CSF can promote the proliferation of erythroid and megakaryocyte progenitor cells. GM-CSF, an 18–22 kD glycoprotein, is produced by a variety of cells, including T-cells, B-cells, macrophages, mast cells, endothelial cells and fibroblasts, in response to immune or inflammatory stimuli.

GM-CSF exerts its effects by interacting with cell surface receptors on specific target cells. The receptor is composed of two chains, GM-CSF-α and GM-CSF-β. L. S. Park et al., 89 *Proc. Natl. Acad. Sci.* 4295 (1992). The GM-CSF-α is specific to GM-CSF, while the GM-CSF-β is identical to the β subunit of the IL-5 and IL-3 receptors. G. Goodall et al., 8 *Growth Factors* 87 (1993). Although neither GM-CSF-α or GM-CSFβ have intrinsic kinase activity, GM-CSF treatment of cells results in rapid tyrosine phosphorylation of multiple proteins. Evidence that GM-CSF operates through a STAT signal transduction system is based upon the observation that GM-CSF rapidly activates in a variety of cell lines phosphotyrosine-containing protein complexes that bind to a GAS-like DNA sequence element. A. C. Larner et al., 261 *Science* 1730 (1993) and P. Lamb et al., 83 *Blood* 2063 (1994). It has been reported that GM-CSF activates STAT5, which is likely a constituent of all of the reported GM-CSF activated complexes. Ihle et al., 11 *Trends in Genetics*, 69 (1995).

Interleukin-3 (IL-3) is a pleiotropic cytokine produced primarily by activated T-cells. Its effects include stimulating the proliferation and differentiation of both pluripotent hematopoietic precursor cells as well a wide variety of lineage committed cells Ihle, J. N. in *Peptide Growth Factors and their Receptors* Springer-Verlag, New York (1991). The mature protein has an apparent molecular weight of 28,000, and binds to a cell surface receptor (IL-3R) that consists of at least two polypeptide chains, IL-3α and IL-3Rβ. The IL-3Rβ chain is also a component of the IL-5 and GM-CSF receptors, whereas the IL-3α chain is unique to the IL-3R. Miyajama et al 82 *Blood* 1960, (1993). Binding of IL-3 to its receptor causes the activation of the tyrosine kinase JAK2 and the rapid tyrosine phosphorylation of a set of cytoplasmic proteins. O. Silvennoinen et al., 90 *Proc. Natl. Acad Sci.* 8429 (1993). A GAS-binding complex that contains a member of the STAT family can be detected in extracts from cells treated with IL-3. A. C. Larner et al., 261 *Science* 1730 (1993); J. N. Ihle et al., 19 *Trends Biochem. Sci.* 222 (1994). It has been reported that IL-3 activates STAT5, which is thus likely a constituent of the reported IL-3-activated complexes. J. N. Ihle et al., 11 *Trends in Genetics*, 69 (1995).

Erythropoietin (Epo) is the major hormone responsible for the proliferation and maturation of red blood cell precursors. S. B. Krantz, 77 *Blood* 419 (1991). In vitro evidence indicates that it also plays a role in thrombocytopoiesis. An et al., 22 *Exp. Hemat.* 149 (1994). The protein, which has an apparent molecular weight of 30,000, is produced mainly in the kidneys and is induced by conditions of tissue hypoxia. It acts by binding to a cell surface receptor (EpoR) that consists of a single polypeptide chain that is a member of the hematopoietin receptor family. A. D'Andrea et al 57 *Cell* 277 (1989). An early event following the binding of Epo to EpoR is the activation of the tyrosine kinase JAK2, which associates non-covalently with the cytoplasmic domain of the receptor chain. B. Witthuhn et al, 74 *Cell* 227. Activation of JAK2 by Epo is correlated with induction of tyrosine phosphorylation of the EpoR and cytoplasmic proteins. Epo treatment of cells also results in the rapid induction of a GAS-binding activity that contains STAT proteins that are thought to contribute to Epo-induced changes in gene expression. P. Lamb et al., 83 *Blood* 2063 (1994); Finbloom et at., 14 *Mol. Cell Biol.* 2113 (1994). It has been reported that Epo activates STAT5, which is thus likely a constituent of the reported Epo-activated complexes. J. N. Ihle et al., 11 *Trends in Genetics*, 69 (1995).

G-CSF is a pleiotropic cytokine best known for its specific effects on the proliferation, differentiation, and activation of hematopoietic cells of the neutrophilic granulocyte lineage. G-CSF has also been reported to have chemotactic activity for human granulocytes and monocytes as well as for mesenchymal cells including fibroblasts, smooth muscle cells and myofibroblasts. These in vitro functions reflect the potential in vivo roles for G-CSF in the maintenance of steady state hematopoiesis, defense against infection, inflammation and repair. When G-CSF was administered to various animal models, an elevation of circulating neutrophils has been observed. G-CSF is now used clinically in patients that have granulopenia as a result of receiving chemotherapy or receiving immunosuppressive agents after organ transplantation. M. A. S. Moore, 9 *Annu. Rev. Immunol.* 159 (1991), N. A. Nicola, 58 *Annu. Rev. Biochem.* 45 (1989), and E. Pimentel, (1994) in *Handbook of Growth Factors, Vol III*, E. Pimentel, ed., CRC Press, Boca Raton, p. 177.

G-CSF exerts its biological activity through binding to G-CSFr. The receptor for G-CSF (G-CSFr) is a member of the type I cytokine receptor superfamily that lacks a kinase domain and appears to consist of a single polypeptide chain. Dimerization of two G-CSFr chains forms a high affinity binding site for G-CSF. Among the various hematopoitin receptor superfamily members, G-CSFr is most closely related to gp 130, the signal-transducing component of the IL-6, oncostatin M, and leukemia inhibitory factor receptors. Recent studies have demonstrated that in myeloid leukemia cell lines, G-CSF treatment results in rapid tyrosine phosphorylation of G-CSFr, JAK1 and JAK2 tyrosine kinases and the members of the STAT family of transcription factors. S. E. Nicholson et al. 91 *Proc. Natl. Acad. Sci. USA* 2985 (1994) and S. S. Tian et. al., 84 *Blood* 1760 (1994).

It has previously been reported that many cytokines, including IL-3, GM-CSF, Epo, G-CSF, IL-4 and IL-13, activate STAT or STAT-like complexes that bind to DNA sequence elements related to the GAS elements that were first characterized in the promoters of IFNγ-responsive genes. However, to date there has been no reported demonstration that the DNA sequences reported to bind to the STAT or STAT-like complexes activated by IL-3, GM-CSF, Epo, G-CSF, IL-4 and IL-13 can mediate transcriptional induction in response to those cytokines. Accordingly, the identification of DNA sequence-elements capable of mediating transcriptional activation in response to cytokines such as IL-4, GM-CSF, G-CSF and Epo, for example, would be useful tools that would allow the responses mediated by various cytokine-activated DNA-binding proteins to be conveniently assayed.

The disclosures of the above-cited references are hereby incorporated by reference in their entirety.

SUMMARY OF THE INVENTION

The present invention is directed to methods for screening for modulators (i.e., agonists and antagonists) of cytokine-mediated transcription, and to the DNA constructs and cytokine-responsive host cell lines transfected with such DNA constructs used in such screening methods. In a preferred embodiment, the present invention is directed to methods for screening for cytokine modulators involved in the STAT5 protein and/or STAT6 protein signaling pathway. In this regard, the DNA constructs of the present invention include oligonucleotide sequences containing regulatory elements that selectively bind activated STAT5 and/or STAT6 proteins, and modulate transcription of the associated heterologous gene, in response to appropriate signaling molecules, such as the cytokines IL-3, IL-4, IL-13, Epo, G-CSF and GM-CSF. Surprisingly, and contrary to the teaching in the art, only a limited subset of the regulatory elements that bind activated STAT5 and/or STAT6 proteins actually modulate transcription of the associated heterologous gene in the assays of the present invention.

In particular, the present invention provides a DNA construct comprising (a) an oligonucleotide sequence comprising a regulatory element of the nucleotide sequence TTN$_x$AA, operably linked to (b) a promoter, operably linked to (c) a heterologous gene, wherein N is independently selected from A, T, C or G and x is 4, 5, 6 or 7, and wherein the DNA construct is operably linked in such a manner that the heterologous gene is under the transcriptional control of the promoter and oligonucleotide sequence when the oligonucleotide sequence is bound by a STAT protein activated in response to IL-2, IL-3, IL-4, IL-7, IL-9, IL-13, G-CSF, GM-CSF, Epo or Tpo. Also provided is a cytokine-responsive host cell transfected with this DNA construct.

The present invention also provides a DNA construct comprising (a) an oligonucleotide sequence comprising a regulatory element of the nucleotide sequence ANT-TCNNNNGAANA (SEQ ID NO. 3) operably linked to (b) a promoter, operably linked to (c) a heterologous gene, wherein N is independently selected from A, T, C or G, and wherein the DNA construct is operably linked in such a manner that the heterologous gene is under the transcriptional control of the promoter and oligonucleotide sequence when the oligonucleotide sequence is bound by a protein complex comprising a STAT6 protein activated in response to a cytokine. Also provided is a cytokine-responsive host cell transfected with this DNA construct.

Further, the present invention provides methods for measuring the ability of a compound to act as an agonist of gene transcription comprising (a) contacting the compound with the transfected host cells described above under conditions in which the heterologous gene is capable of being expressed in response to the compound, and (b) comparing the level of gene expression in step (a) with the level of gene expression from the host cells in the absence of the compound. Alternatively, the present invention also provides a method for measuring the ability of a compound to act as an antagonist of gene transcription comprising (a) contacting the compound with the transfected host cells described above in the presence of a predetermined amount of a cytokine under conditions in which the heterologous gene is capable of being expressed in response to the cytokine, and (b) comparing the level of gene expression in step (a) with the level of gene expression from the host cells in the presence of the cytokine, but the absence of the compound. In both these methods, the heterologous gene may be any appropriate reporter gene such as the heterologous gene for luciferase, chloramphenicol acetyl transferase, green fluorescent protein or β-galactosidase.

These and various other advantages and features of novelty which characterize the invention are pointed out with particularity in the claims annexed hereto and forming a part hereof. However, for a better understanding of the invention, its advantages, and objects obtained by its use, reference should be had to the accompanying drawings and descriptive matter, in which there is illustrated and described preferred embodiments of the invention.

DEFINITIONS

For the purposes of this invention:

"Oligonucleotide" or "DNA" molecule or sequence refers to a molecule comprised of the deoxyribonucleotides adenine (A), guanine (G), thymine (T) and/or cytosine (C), in either single-stranded form or a double-stranded helix, and comprises or includes a "regulatory element" according to the present invention, as that term is defined herein. The exact size, strandedness and orientation (i.e. 3' to 5', or 5' to 3') will depend upon many factors, which, in turn, depend upon the ultimate function and use of the oligonucleotides of the present invention. Thus, the term "oligonucleotide" or "DNA" includes double-stranded DNA found in linear DNA molecules or fragments, viruses, plasmids, vectors, chromosomes or synthetically derived DNA. As used herein, particular double-stranded DNA sequences may be described according to the normal convention of giving only the sequence in the 5' to 3' direction.

"Regulatory element" refers to a deoxyribonucleotide sequence comprising the whole, or a portion of, an oligonucleotide sequence to which an activated transcriptional regulatory protein, or a complex comprising one or more activated transcriptional regulatory proteins, binds so as to transcriptionally modulate the expression of an associated gene or genes, including heterologous genes.

"Signaling molecule" refers to an extracellular polypeptide, oligosaccharide or other non-peptidyl molecule, in either a free or bound form, that interacts with a receptor at or near the surface of a cell. This interaction in turn triggers an intracellular pathway which includes the activation of one or more transcriptional regulatory proteins that bind to a regulatory element, thereby transcriptionally modulating the expression of an associated gene or genes. As used herein, "signaling molecule" includes naturally occurring molecules, such as cytokines, peptidyl and non-peptidyl hormones, antibodies, cell-surface antigens, or synthetic mimics of any of these signaling molecules, or synthetic molecules that mimic the action of any of these signaling molecules.

"Cytokines" refer to a diverse grouping of soluble polypeptides, including growth factors and hormones, that control the growth, differentiation and function of cells in such a manner as to ultimately elicit a phenotypic response in an organism. Preferred cytokines useful with the regulatory elements and associated methods of the present invention include IL-3, IL-4, IL-13, GM-CSF, G-CSF, Epo and Tpo.

"Transcriptional regulatory protein" refers to cytoplasmic or nuclear proteins that, when activated, bind the regulatory elements/oligonucleotide sequences of the present invention either directly, or indirectly through a complex of transcriptional regulatory proteins or other adapter proteins, to transcriptionally modulate the activity of an associated gene or genes. Thus, transcriptional regulatory proteins can bind directly to the DNA regulatory elements of the present invention, or can bind indirectly to the regulatory elements by binding to another protein, which in turn binds to or is bound to a DNA regulatory element of the present invention. See e.g., S. A. Veals et al., 13 Molec. Cell. Biol., 196–206 (1993). As used herein, transcriptional regulatory proteins, include, but are not limited to, those proteins referred to in the art as STAT proteins (Z. Zhong et al., 264 Science, 95) STF proteins (C. Schindler et al., 13 EMBO J., 1350 (1994)), Mammary Gland-Specific Nuclear Factor (M. Schmidt-Ney et al., 6 Mol. Endochronol., 988 (1992) and H. Wakao et al., 267 J. Biol. Chem., 16365 (1992)), APRF (Wegenka, 13 Mol. Cell Bio., 276), GHIF (Mayer, 269 J. Biol. Chem., 4701), GHSF and EPOSF (Finbloom, 14 Mol. Cell Bio., 2113), as well as to all substantially homologous analogs and allelic variations thereof.

"Transcriptionally modulate the expression of an associated gene or genes" means to change the rate of transcription of such gene or genes.

"STAT protein" refers to those transcriptional regulatory proteins designated as "Signal Transducers and Activators of Transcription" (STAT) by Dr. J. E. Darnell of Rockefeller University. See Zhong, 264 Science 95. As used herein, STAT proteins include the p91 (STAT1), p84 (STAT1), p113 (STAT2) proteins and the STAT-associated p48 family of proteins. S. A. Veals et al., 12 Mol. Cell. Biol., 3315 (1992). Further, STAT proteins also include a binding protein designated as STAT3 (Zhong, 264 Science 95), and a binding protein designated as STAT4 (Id.). In addition, MGF is now renamed STAT5 (Gouilleux et al., 13 EMBO J., 4361–4369 (1994)) and STAT-IL-4 (or STAT6) has recently been cloned. Hou et al., 265 Science, 730 (1994) and J. N. Ihle et al. 11 Trends in Genetics, 69 (1995). Also included are substantially homologous analogs and allelic variations of all of the above STAT proteins.

"Activate", "activated", "activation" or derivatives thereof, means that one or more transcriptional regulatory proteins within a cell are modified post-translationally, or are constituitively active, such that they can bind directly or indirectly to DNA regulatory elements/oligonucleotide sequences of the present invention in a sequence-specific manner. This modification will typically comprises phosphorylation of the transcriptional regulatory proteins via a variety of mechanisms, including, but not limited to activation by various protein kinases. See, e.g., (Shuai, 258 Science, 1808 an P. Cohen, 17 TIBS, 408 (1992)).

"DNA construct" refers to any genetic element, including, but not limited to, plasmids, vectors, chromosomes and viruses, that incorporate the oligonucleotide sequences of the present invention. For example, the DNA construct can be a vector comprising a promoter that is operably linked to an oligonucleotide sequence of the present invention, which is in turn, operably linked to a heterologous gene, such as the gene for the luciferase reporter molecule.

"Promoter" refers to a DNA regulatory region capable of binding directly or indirectly to RNA polymerase in a cell and initiating transcription of a downstream (3' direction) coding sequence. For purposes of the present invention, the promoter is bounded at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S 1 nuclease), as well as protein binding domains (consensus sequences) responsible for the binding of RNA polymerase. Eukaryotic promoters will often, but not always, contain "TATA" boxes and "CCAT" boxes. Prokaryotic promoters contain Shine-Daigarno sequences in addition to the −10 and −35 consensus sequences.

"Gene" refers to a nucleic acid molecule, the sequence of which includes all the information required for the normal regulated production of a particular protein. A "heterologous" region of a DNA construct (i.e. a heterologous gene) is an identifiable segment of DNA within a larger DNA construct that is not found in association with the other genetic components of the construct in nature. Thus, when the heterologous gene encodes a mammalian gene, the gene will usually be flanked by a promoter that does not flank the structural genomic DNA in the genome of the source organism.

A promoter of a DNA construct, including an oligonucleotide sequence according to the present invention, is "operably linked" to a heterologous gene when the presence of the promoter influences transcription from the heterologous gene, including genes for reporter sequences such as luciferase, chloramphenicol acetyl transferase, -galactosidase and secreted placental alkaline phosphatase. Operably linked sequences may also include two segments that are transcribed onto the same RNA transcript. Thus, two sequences, such as a promoter and a "reporter sequence" are operably linked if transcription commencing in the promoter will produce an RNA transcript of the reporter sequence. In order to be "operably linked" it is not necessary that two sequences be immediately adjacent to one another.

A host cell has been "transfected" by exogenous or heterologous DNA (e.g. a DNA construct) when such DNA has been introduced inside the cell. The transfecting DNA may or may not be integrated (covalently linked) into chromosomal DNA making up the genome of the cell. In prokaryotes, yeast, and mammalian cells for example, the transfecting DNA may be maintained on an episomal element such as a plasmid. With respect to eukaryotic cells, a stably transfected cell is one in which the transfecting DNA has become integrated into a chromosome so that it is inherited by daughter cells through chromosome replication. This stability is demonstrated by the ability of the eukaryotic cell to establish cell lines or clones comprised of a population of daughter cells containing the transfecting DNA.

"Cytokine-responsive host cell" refers to a cell line that expresses, either normally or after transfection of the requisite cDNAs, the relevant cytokine receptor components, JAK proteins, STAT proteins, and accessory factors such that, upon cytokine binding to the cell surface, STAT-mediated gene transcription is affected.

BRIEF DESCRIPTION OF THE DRAWING

The invention may be further illustrated by reference to the accompanying Drawing wherein.

DETAILED DESCRIPTION OF EMBODIMENTS OF THE INVENTION

Figure 1A:
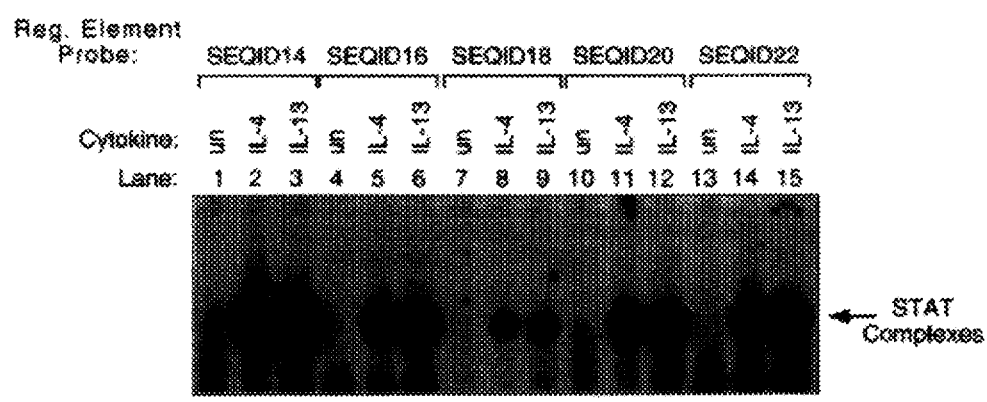
FIG. 1A and 1B are a reproduction of Electrophoretic Mobility Shift Assay (EMSA) autoradiograms that show the binding patterns of transcriptional regulatory protein-DNA DNA binding complexes activated by IL-4 and IL-13. The EMSA's were performed as described in the Examples herein. The radiolabeled, double-stranded oligonucleotide probes utilized in the EMSAs of FIGS. 1A and 1B were made by annealing the oligonucleotides of SEQ ID NOs. 14–23 (FIG. 1A) and 24–35 (FIG. 1B).

The present inventors have discovered that only a select group of regulatory elements that bind activated transcriptional regulatory proteins, such as STAT proteins, actually modulate the transcription of an operably linked heterologous gene in a cell-based screen. This unexpected result is in direct contradiction to the teaching in the art that a regulatory element that binds such activated transcriptional regulatory proteins will also activate the transcription of an associated gene. Thus, the binding of a regulatory element to an activated transcriptional regulatory protein is not correlated, and provides no predictability, with respect to those regulatory elements that will activate transcription of an associated gene in response to this binding. It is only through the teaching of the present inventors that one will be able to select, without resorting to undue experimentation, regulatory elements/oligonucleotide sequences that will both bind to, and cause transactivation from, activated transcriptional regulatory proteins, such as STAT proteins.

The oligonucleotide sequences, comprising DNA regulatory elements, and that are incorporated into the DNA constructs of the present invention are selected from the nucleotide sequence TTN$_x$AA, wherein N is independently selected from A, T, C or G and x is 4, 5, 6 or 7. More preferably, the regulatory elements comprise oligonucleotide sequences that bind and transactivate in response to activated STAT5 and/or STAT6 proteins. These preferred oligonucleotides sequences are selected from the group consisting of TTCNNNGAA (SEQ ID NO. 1), TTCNNNNGAA (SEQ ID NO.2) and ANT-TCNNNNGAANA (SEQ. ID NO. 3), including their double stranded complements, where N is independently selected from A, T, C or G. Especially preferred oligonucleotide sequences according to the present invention include: ACT-TCCCAAGAACA (SEQ ID NO. 4), ACTTCCCCG-GAACA (SEQ ID NO. 5), ACTTCCCCAGAACA (SEQ ID NO. 6), ACTTCCCAGGAACA (SEQ ID NO. 7), ACTTC-CTAAGAACA (SEQ ID NO.8), ACTTCTTAAGAACA (SEQ ID NO.9), TTCCCGGAA (SEQ ID NO. 10), TTC-CCCGAA (SEQ ID NO. 11 ), TTCTAAGAA (SEQ ID NO. 12) and TTCTCAGAA (SEQ ID NO. 13).

The oligonucleotide sequences of the DNA constructs of the present invention can comprise the entire regulatory element alone, or can include additional flanking nucleotide sequences. In this regard, it is preferable that such oligonucleotide sequences comprise between 8 and 200 nucleotides, including the regulatory elements of the present invention. However, sequences in excess of 200 nucleotides that contain such regulatory elements, and that are capable of binding activated transcriptional regulatory proteins, and of transcriptionally modulating the expression of one or more genes thereby, are also considered to be within the scope of the present invention.

The oligonucleotide sequence component of the DNA constructs of the present invention can also comprise multireefs of two or more "units" of the basic regulatory elements. In this regard, such multimer oligonucleotide sequences can, as a practical matter, contain from about 2 to 15 units of the same or different regulatory elements according to the present invention. However, theoretically, there is no limit to the number of regulatory elements within such a multimer oligonucleotide sequence. When used in the DNA construct, including a promoter and heterologous gene, according to the present invention, a multimer of the regulatory elements can enhance the expression of the gene from the DNA construct in response to various cytokines or other signaling molecules.

A variety of signaling molecules activate transcriptional regulatory proteins that bind directly or indirectly to the DNA constructs of the present invention, and modulate transcription of the operably linked heterologous gene. Nonlimiting examples of such signaling molecules include polypeptides such as cytokines and antibodies, and cell-surface antigens, oligosaccarides typically found at or near the surface of cell, non-peptidyl molecules such as TUBag4 (P. Constant et al., 264 Science, 267 (1994)) and synthetic mimics any of these molecules, in both their free and bound forms. Thus, the present invention includes cell to cell or cell to substrate transcriptional regulatory protein activation via signaling molecules bound to or near the surface of a cell or other substrate.

Preferably, the signaling molecules according to the present invention comprise cytokines that activate transcriptional regulatory proteins, such as STAT proteins, that bind to the regulatory elements/oligonucleotide sequences of the present invention. Examples of such cytokines include, but are not limited to, Interleukins 2, 3, 4, 5, 6, 7, 9, 10, 11, 12, 13 and 15 (IL-2, IL-3, IL-4, IL-5, IL-6, IL-7, IL-9, IL-10, IL-11, IL-12, IL-13 and IL-15), granulocyte-macrophage colony stimulating factor (GM-CSF), granuloctyte colony stimulating factor (G-CSF), colony stimulating factor 1 (CSF-1), interferons alpha, beta, and gamma (IFNα, IFNβ, IFNγ), epidermal growth factor (EGF), platelet derived growth factor (PDGF), leukemia inhibitory factor (LIF), Oncostatin M, nerve growth factor (NGF), ciliary neurotrophic factor (CNTF), brain-derived neurotrophic factor (BDNF), erythropoietin (Epo), thrombopoietin (Tpo), growth hormone and prolactin. Particularly preferred cytokines according to the present invention include those that activate the STAT5 protein and/or STAT6 protein pathways, including, but are not limited to, IL-2, IL-3, IL-4, IL-5, IL-7, IL-9, IL-13, IL-15, G-CSF, GM-CSF, Epo, Tpo and growth hormone.

The recombinant DNA construct, such as a reporter plasmid, according to the present invention, can be constructed using conventional molecular biology, microbiology, and recombinant DNA techniques well known to those of skill in the art. Such techniques are explained fully in the literature, including Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins, eds. (1984)]; "Animal Cell Culture" [R. I. Freshney, ed. (1986)]; "Immobilized Cells and Enzymes" [IRL Press, (1986)] and B. Perbai, "A Practical Guide to Molecular Cloning" (1984), the disclosures of which are herein incorporated by reference.

Promoter sequences useful in DNA constructs according to the present invention include all prokaryotic, eukaryotic or vital promoters capable of driving transcription of a heterologous gene of interest in combination with a regulatory element of the present invention, when transfected into an appropriate host cell. Suitable prokaryotic promoters include, but are not limited to, promoters recognized by the T4, T3, Sp6, and T7 polymerases, the $P_R$ and $P_L$ promoters of bacteriophage, the transcriptional regulatory protein, recA, heat shock, and lacZ promoters of E. coli, the amylase and the −28-specific promoters of B. subtilis, the promoters of the bacteriophages of Bacillus, Streptomyces promoters, the int promoter of bacteriophage, the bla promoter of the β-lactamase gene of pBR322 and the CAT promoter of the chloramphenicol acetyl transferase gene of pPR325. See, e.g., B. R. Glick, 1 J. Ind. Microbiol., 277–282 (1987); Y. Cenatiempo, 68 Biochimie, 505–516 (1986); J. D. Watson et al., In: Molecular Biology of the Gene, Fourth Edition, Benjamin Cummins, Melo Park, Calif. (1987) and. S. Gottesman, 18 Ann. Rev. Genet., 415–442 (1984), the disclosures of which are herein incorporated by reference. Preferred eukaryotic promoters include the yeast cyc-1 promoter, the promoter of the mouse metallothionein I gene, the thymidine kinase promoter of the Herpes simplex virus, the SV40 early promoter, and the yeast gal-4 gene promoter. See Guarante et al., 78 Proc. Natl. Acad. Sci. USA, 2199–2203 (1981), D. Hamer et al., 1 J. Mol. Appl. Gen., 273–288 (1982), S. McKnight, 31 Cell, 355–365 (1982), C. Benoist et al., 290 Nature (London), 304–310 (1981), S. A. Johnston et al., 79 Proc Natl. Acad. Sci. (U.S.A.), 6971–6975 (1982) and P. A. Silver et al., 81 Proc. Natl. Acad. Sci. (U.S.A.), 5951–5955 (1984), the disclosures of which are herein incorporated by reference herein. Preferably, a DNA construct according to the present invention utilizes the thyroidinc kinase gene promoter of the Herpes simplex virus.

The third component of the recombinant DNA or construct molecules of the present invention is a "heterologous gene" which may be composed of any set of nucleotides regardless of sequence. Nonlimiting examples of such heterologous genes include the structural genes for luciferase, β-galactosidase, chloramphenicol acetyl transferase, secreted placental alkaline phosphatase, human growth hormone, tPA, green fluorescent protein and interferon. For a more extensive list of heterologous genes usable in the constructs and methods of the present invention, see Beaudet, 37 Am. J. Hum. Gem, 386–406 (1985).

Preferably the heterologous gene comprises a reporter gene whose product is used to assess regulation of transcription via a promoter and a regulatory element/oligonucleotide sequence of the present invention. The expression of this "reporter sequence" results in the formation of a reporter product (e.g., protein) which is readily detectable. The reporter sequence will preferably be selected such that the reporter molecule will have a physical and chemical characteristics which will permit or facilitate its identification or detection by means well known in the art. In one embodiment, the presence of the reporter molecule will be detected through the use of an antibody or an antibody fragment, capable of specific binding to the reporter molecule. In another embodiment, a reporter such as β-galactosidase or luciferase can be assayed enzymatically or immunologically.

A preferred reporter molecule is LUC, well known in the art. See, e.g., J. R. De-Wet et al., 7 Mol. Cell Bio., 725 (1987). Because this is an insect gene, it is absent from mammalian cells and the enzyme product can be directly assayed in a cell extract. The level of enzyme activity corresponds to the amount of enzyme that was made, which in turn reveals the level of expression. In addition, LUC mRNA may also be measured directly.

Typically, a plasmid containing the recombinant DNA molecule of the present invention, including the LUC gene, is introduced into cytokine-responsive mammalian cells, which are then grown to, at or near confluency. In this regard, any cytokine-responsive host cell capable of activating one or more transcriptional regulatory proteins in response to an appropriate signaling molecule or molecules can be transfected with the DNA constructs of the present invention. Preferably, such cytokine-responsive host cells comprise mammalian cells, such as HepG2, U937, ME-180, TF-1 and NFS-60 cells.

The reporter cells are treated with a compound or sample suspected of containing a signaling molecule capable of inducing or activating a transcriptional regulatory protein, for example, an extract of other cytokine-treated cells. The LUC-producing reporter cells are extracted, and the soluble extracts are supplemented with luciferin and ATP. In the presence of these compounds the action of luciferase generates light, which is detected using a luminometer. The amount of light produced is directly related to the amount of luciferase present in the cellular extract.

With a suitable DNA construct of the present invention transfected into a cytokine-responsive host cell, the present invention provides a convenient means for measuring the transcriptional activity of a reporter product in response to a signaling molecule, such as a cytokine or extract of cytokine-treated cells.

Importantly, when transcription of LUC is activated by the transcriptional regulatory protein being assayed, LUC synthesis is increased relative to a control lacking the transcriptional regulatory protein. Thus, the amount of LUC enzyme produced is an indirect measure of transcription induced by the activated transcriptional regulatory protein binding to the regulatory elements/oligonucleotide sequences of the present invention which is operably linked to the LUC gene.

When a preferred cytokineoresponsive host cell, such as a HepG2 cell, is transfected with a reporter DNA construct according to the present invention, it can be utilized in assays to detect agonists and antagonists of signaling molecules that induce gene transcription via activated transcriptional regulatory proteins. As used herein, agonists or antagonists of gene transcription include compounds that intervene at any point within the signaling pathway from interaction between the signaling molecule and a cell surface receptor through activation of one or more transcriptional regulatory proteins and binding of the same to DNA regulatory elements, the end result of which is modulation of gene transcription. Further, as used herein, agonists and antagonists of gene transcription also include potentiators of known compounds with such agonist or antagonist properties. Agonists can be detected by contacting the transfected host cell with a compound or mix of compounds and, after a fixed period of time, determining the level of gene expression (e.g., the level of luciferase produced) within the treated cells. This expression level can then be compared to the expression level of the reporter gene in the absence of the compound(s). The difference between the levels of gene expression, if any, indicated whether the compound(s) of interest agonize the activation of intracellular transcriptional regulatory proteins in an analogous fashion to a known agonist signaling molecule, such as a cytokine. Further, the magnitude of the level of reporter product expressed between the treated and untreated cells provides a relative indication of the strength of that compound(s) as an agonist of gene transcription via a transcriptional regulatory protein pathway.

Alternatively, such a transfected host cell can be used to find antagonists of known agonists, e.g., cytokines such as IL-4, of gene transcription utilizing host cells transfected with the DNA constructs according to the present invention. In such an assay, the compound or compounds of interest are contacted with the host cell in conjunction with one or more known agonists (e.g., cytokines) held at a fixed concentration. The extent to which the compound(s) depress the level of gene expression in the host cell below that available from the host cell in the absence of compounds, but presence of the known agonist, provides an indication and relative strength of the antagonist properties of such compound(s).

Thus, the present invention provides methods to assay for agonists and antagonists of gene transcription utilizing the regulatory elements/oligonucleotides of the DNA constructs and transfected host cells of the present invention. Further, the agonist and antagonist compounds discovered utilizing these methods can serve as pharmaceutical agents in the intervention of various cytokine-induced disease states and conditions, or to ameliorate disease states caused by cytokine deficiency, such as inflammation, infection, anemia, cytopenia and cancerous or precancerous conditions.

The invention will be further illustrated by reference to the following non-limiting Examples.

EXAMPLE 1

Reagents

Oligonucleotides were obtained from Operon Technologies (Alameda, Calif.). Recombinant human GM-CSF, IL-3, IL-4 and IL-6 were obtained from R & D Systems (Minneapolis, Minn.). Recombinant human IL-13 was obtained from Biosource (Camarillo, Calif.). Recombinant human Epo and G-CSF were from Amgen, Inc. (Thousand Oaks, Calif.). Protease inhibitors and poly d(I-C) poly d(I-C) were from Boehringer Mannheim (Indianapolis, Ind.).

Cells and cell culture

U937 cells were obtained from Dr. J. E. Darnell (commercially available from ATCC) and grown in RPMI-1640 (BioWhittaker) supplemented with fetal bovine serum (10% v/v), glutamine (2 mM) and gentamicin sulfate (50 µg/mL). ME-180 cells were obtained from the ATCC and grown in McCoy's 5A (Gibco/BRL, Gaithersburg, Md.) supplemented with fetal bovine serum (10% v/v), glutamine (2 mM) and gentamicin sulfate (50 µg/mL). TF-1 cells were obtained from the ATCC and grown in RPMI-1640 (BioWhittaker) supplemented with fetal bovine serum (10% v/v), glutamine (2 mM), gentamicin sulfate (50 µg/mL), and GM-CSF (5 ng/mL). IL-3-dependent NFS-60 cells were obtained from Dr. J. N. Ihle (St. Jude Children's Research Hospital, Memphis, Tenn.) and were maintained in RPMI-1640 supplemented with fetal bovine serum (10% v/v), glutamine (2 mM), gentamicin sulfate (50 µg/mL) and 10% WEHI-3B-conditioned medium (to provide IL-3). Factor-independent NFS-60 cells were selected by withdrawing WEHI-3B-conditioned medium from the culture medium. In about two weeks, the cells adjusted to the new growth conditions and proliferated as well as the parental NFS-60 cells. ME-180 cells were treated with cytokines at 50–75% confluency, U937, TF-1 and NFS-60 cells at a density of $2 \times 10^5 - 1 \times 10^6$/ml. Cytokines were used at the following concentrations: IL-6, 10 ng/mL, IL-4, 10–30 ng/ml, GM-CSF, 5 ng/ml, Epo, 4–6 U/mL, IL-3, 15–20 ng/mL, IL-13, 60 ng/mL, and G-CSF, 20 ng/mL.

Preparation of nuclear extracts and Electrophoretic Mobility Shift Assays

Nuclear extracts were prepared by NP40 lysis as described in H. B. Sadowski and M. Z. Gilman, 362 *Nature*, 79 (1993), the disclosure of which is herein incorporated by reference. Protein concentrations were measured using Bradford dye binding assay (Bio-Rad Laboratories, Hercules, Calif.). Nuclear extracts were prepared either from untreated U937 cells, U937 cells treated for 30 min with GM-CSF, U937 cells treated for 30 min with IL-4, TF-1 cells starved of GM-CSF for 18 h and then either left untreated or treated for 30 min with Epo, IL-3 or GM-CSF; ME-180 cells either left untreated or treated for 30 min with IL-4 or IL-13; or NFS-60 cells starved of IL-3 for 16–18 h then either left untreated or treated for 10 min with G-CSF, IL-3 or IL-6. The double-stranded probe oligonucleotides used in the Electrophoretic Mobility Shift Assays (EMSAs) were formed by annealing oligonucleotides with the sequences:

| | |
|---|---|
| 5'-GATCCACTTCCCAAGAACAGA-3' | (SEQ ID NO. 14) |
| 3'-GTGAAGGGTTCTTGTCTCTAG-5' | (SEQ ID NO. 15) |
| 5'-GATCTGCTTCCCCGGAACGT-3' | (SEQ ID NO. 16) |
| 3'-ACGAAGGGGCCTTGCACTAG-5' | (SEQ ID NO. 17) |
| 5'-GATCTGCTTCCCCAGAACGT-3' | (SEQ ID NO. 18) |
| 3'-ACGAAGGGGTCTTGCACTAG-5' | (SEQ ID NO. 19) |
| 5'-GATCTGCTTCCCAAGAACGT-3' | (SEQ ID NO. 20) |
| 3'-ACGAAGGGTTCTTGCACTAG-5' | (SEQ ID NO. 21) |
| 5'-GATCCACTTCCCCGGAACAGA-3' | (SEQ ID NO. 22) |
| 3'-GTGAAGGGGCCTTGTCTCTAG-5' | (SEQ ID NO. 23) |
| 5'-GATCCACTTCCCCAGAACAGA-3' | (SEQ ID NO. 24) |
| 3'-GTGAAGGGGTCTTGTCTCTAG-5' | (SEQ ID NO. 25) |
| 5'-GATCCACTTCCCAGGAACAGA-3' | (SEQ ID NO. 26) |
| 3'-GTGAAGGGTCCTTGTCTCTAG-5' | (SEQ ID NO. 27) |
| 5'-GATCTACTTCCCAAGAACATA-3' | (SEQ ID NO. 28) |
| 3'-ATGAAGGGTTCTTGTATCTAG-5' | (SEQ ID NO. 29) |
| 5'-GATCCGCTTCCCAAGAACGGA-3' | (SEQ ID NO. 30) |
| 3'-GCGAAGGGTTCTTGCCTCTAG-5' | (SEQ ID NO. 31) |
| 5'-GATCCACTTCTTAAGAACAGA-3' | (SEQ ID NO. 32) |
| 3'-GTGAAGAATTCTTGTCTCTAG-5' | (SEQ ID NO. 33) |
| 5'-GATCCACTTTCCAAGAACAGA-3' | (SEQ ID NO. 34) |
| 3'-GTGAAAGGTTCTTGTCTCTAG-5' | (SEQ ID NO. 35) |
| 5'-GATCTGCTTCCCGGAACGT-3' | (SEQ ID NO. 36) |
| 3'-ACGAAGGGCCTTGCACTAG-5' | (SEQ ID NO. 37) |
| 5'-GATCGATTTCCCCGAAATG-3' | (SEQ ID NO. 38) |
| 3'-CTAAAGGGGCTTTACCTAG-5' | (SEQ ID NO. 39) |
| 5'-GATCATATTCCTGTAAGTG-3' | (SEQ ID NO. 40) |
| 3'-TATAAGGACATTCACCTAG-5' | (SEQ ID NO. 41) |
| 5'-GATCATATTCCCGTAAGTG-3' | (SEQ ID NO. 42) |
| 3'-TATAAGGGCATTCACCTAG-5' | (SEQ ID NO. 43) |
| 5'-GATCCATTTCTGGAAATG-3' | (SEQ ID NO. 44) |
| 3'-GTAAAGACCTTTACCTAG-5' | (SEQ ID NO. 45) |
| 5'-GATCCATTTCCCGTAAATC-3' | (SEQ ID NO. 46) |
| 3'-GTAAAGGGCATTTAGGATC-5' | (SEQ ID NO. 47) |
| 5'-GATCATATTACCAGAAATG-3' | (SEQ ID NO. 48) |
| 3'-TATAATGGTCTTTACCTAG-5' | (SEQ ID NO. 49) |
| 5'-GATCATTTTCCAGTAACAG-3' | (SEQ ID NO. 50) |
| 3'-TAAAAGGTCATTGTCCTAG-5' | (SEQ ID NO. 51) |
| 5'-GATCCAATTTCTAAGAAAGGA-3' | (SEQ ID NO. 52) |
| 3'-GTTAAAGATTCTTTCCTCTAG-5' | (SEQ ID NO. 53) |
| 5'-GATCTGCTTCCCGAACGT-3' | (SEQ ID NO. 54) |
| 3'-ACGAAGGGCTTGCACTAG-5' | (SEQ ID NO. 55) |
| 5'-GATCTGCTTCTCAGAACGT-3' | (SEQ ID NO. 56) |
| 3'-ACGAAGAGTCTTGCACTAG-5' | (SEQ ID NO. 57) |
| 5'-GATCTGCTTCCCCGAACGT-3' | (SEQ ID NO. 58) |
| 3'-ACGAAGGGGCTTGCACTAG-5' | (SEQ ID NO. 59) | where the nucleotide sequences shown in bold type face correspond to nucleotide sequences, including their double-stranded complement, tested for activity as regulatory elements according to the present invention.

The annealed oligonucleotides were labeled by filling in the overhanging ends with Klenow fragment (Boehringer Mannheim) in the presence of [α-$^{32}$P]-dGTP and/or [α-$^{32}$P]-dATP (Amersham Corporation, Arlington Heights, Ill.). Electrophoretic mobility shift assays (EMSA's) were performed in HEPES buffer (13 mM, pH 7.6, Sigma Chemical, St. Louis, Mo.), containing sodium chloride (80 mM), sodium fluoride (3 mM), sodium molybdate (3 mM), DTT (1 mM), EDTA (0.15 mM), EGTA (0.15 mM), glycerol (8% v/v, including contributions from the nuclear extract), poly d(I-C) poly d(I-C) (75 µg/mL), radiolabeled probe (approximately 0.2 ng) and nuclear extract containing 5–10 µg of total protein. Reactions were incubated at room temperature for 20 minutes then resolved on 5% polyacrylamide gels containing 0.25×TBE [1×TBE is Tris borate (89 mM), pH 8.0 containing EDTA (1 mM)] and glycerol (5% v/v). Gels were run at 4° C. in 0.25×TBE at 20V/cm, then dried and autoradiographed.

Relative binding affinities, as determined from the EMSA results for oligonucleotide SEQ ID NOs 14–59, were visually rated and assigned according to the following scale:

(−) band corresponding to specific complex on the EMSA autoradiogram (See e.g., FIG. 1A, lane 7) barely discernible or not discernible.

(+) band corresponding to specific complex on the EMSA autoradiogram (See e.g., FIG. 1A, lanes 8 and 9) easily discernible but of weak intensity.

(++) band corresponding to specific complex on the EMSA autoradiogram (See e.g., FIG. 1A, lanes 5 and 6) easily discernible and of moderate intensity.

(+++) band corresponding to specific complex on the EMSA autoradiogram (See e.g., FIG. 1A, lanes 2 and 3) easily discernible and of strong intensity.

This visual rating system is sufficient to analyze distinguishable differences and trends in the EMSA binding data as opposed to specific numerical values. If desired, the use of a phosphor imager or densitometer (commercially available from e.g., Bio-Rad Laboratories) could provide a means to assess the differences described here quantitatively. Specific visual ratings of binding affinities for the regulatory elements of oligonucleotide SEQ ID NOs 14–41,44–53 and 56–59 are shown in Table 1 below. Specific visual ratings of binding affinities for the regulatory elements of oligonucleotide SEQ ID NOs 36–57 are shown in Table 2 below.

TABLE 1

Relative EMSA binding affinities for a series of regulatory elements of double stranded configurations differing in flanking and spacing sequences to transcriptional regulatory proteins activated in response to the cytokines IL-4 and IL-13 in U-937 or ME-180 cells.

| SEQ ID | Core Regulatory Element | IL-4 | IL-13 |
|---|---|---|---|
| 14 | CACTTCCCAAGAACAGA | +++ | +++ |
| 16 | TGCTTCCCCGGAACGT | ++ | ++ |
| 18 | TGCTTCCCCAGAACGT | + | + |
| 20 | TGCTTCCCAAGAACGT | ++ | ++ |
| 22 | CACTTCCCCGGAACAGA | ++ | ++ |
| 24 | CACTTCCCCAGAACAGA | ++ | ++ |
| 26 | CACTTCCCAGGAACAGA | ++ | ++ |
| 28 | TACTTCCCAAGAACATA | ++ | ++ |
| 30 | CGCTTCCCAAGAACGGA | ++ | ++ |
| 32 | CACTTCTTAAGAACAGA | ++ | ++ |
| 34 | CACTTTCCAAGAACAGA | ++ | ++ |
| 36 | TGCTTCCCGGAACGT | ++ | ++ |
| 38 | GATTTCCCCGAAATG | ++ | ++ |
| 40 | ATATTCCTGTAAGTG | + | n.d. |
| 44 | CATTTCTGGAAATG | ++ | n.d. |
| 46 | CATTTCCCGTAAATC | ++ | n.d. |
| 48 | ATATTACCAGAAATG | + | n.d. |
| 50 | ATTTTCCAGTAACAG | + | n.d. |
| 52 | CAATTTCTAAGAAAGGA | ++ | n.d. |
| 56 | TGCTTCTCAGAACGT | ++ | ++ |
| 58 | TGCTTCCCCGAACGT | ++ | n.d. | n.d. = not determined

TABLE 2

Relative EMSA binding affinities for a series of regulatory elements of double stranded configurations differing in flanking and spacing sequences to transcriptional regulatory proteins activated in response to the cytokines IL-3, GM-CSF, G-CSF.

| SEQ ID No. | GM-CSF | Epo | IL-3 | G-CSF (complex 1) | G-CSF (complex 2) |
|---|---|---|---|---|---|
| 36 | ++ | + | ++ | ++ | ++ |
| 38 | +++ | +++ | +++ | +++ | +++ |
| 40 | + | + | ++ | n.d. | n.d. |
| 42 | + | n.d. | + | n.d. | n.d. |
| 44 | ++ | n.d. | + | n.d. | n.d. |
| 46 | ++ | + | ++ | ++ | ++ |
| 48 | + | + | ++ | n.d. | n.d. |
| 50 | + | n.d. | + | n.d. | n.d. |
| 52 | ++ | +++ | +++ | n.d. | n.d. |
| 54 | − | n.d. | − | +++ | − |
| 56 | ++ | + | ++ | − | ++ | n.d. = not determined

The data in Table 1 show that the IL-4- and IL-13-activated STAT complexes can bind to all of the listed sequences of general structure TTN$_6$AA with similar affinity (with the exception of SEQ ID NO. 18, which was slightly lower in affinity). The IL-4 and IL-13-activated STAT complexes can also bind to all of the listed sequences of general structure TTN$_5$AA with varying affinities.

Figure 1B:
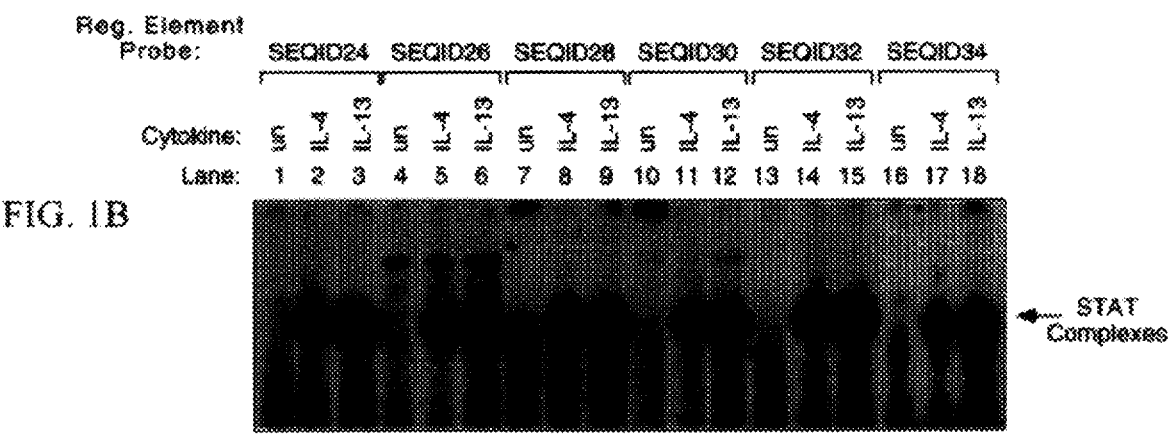

A specific example of the data summarized in Table 1 can be seen with respect to the EMSA autoradiograms of FIGS. 1A and 1B. In panel 1A, radiolabeled, double-stranded oligonucleotide probes made by annealing the oligonucleotides of SEQ ID NOs. 14–23 were used. Lanes marked 'UN' represent experiments using extracts from untreated cells. Other lanes are marked according to the inducing cytokine. Activated complexes can be identified by their absence in untreated extracts and their presence in extracts treated by cytokine. The STAT complexes activated by IL-4 and IL-13 bound to all of the oligonucleotide probes with similar affinities (except SEQ ID NO. 18, which bound with a slightly lower affinity), as can be seen in Lanes 2, 3, 5, 6, 8, 9, 11, 12, 14 and 15 of panel 1A. In panel 1B, radiolabeled, double-stranded oligonucleotide probes made my annealing oligonucleotides of SEQ ID NOs. 24–35 were used. Lanes marked 'UN' represent experiments using extracts from untreated cells. Other lanes are marked according to the inducing cytokine. Activated complexes can be identified by their absence in untreated extracts and their presence in extracts treated by cytokine. The STAT complexes activated by IL-4 and IL-13 bound to all of the oligonucleotide probes with similar affinities, as can be seen in Lanes 2, 3, 5, 6, 8, 9, 11, 12, 14, 15, 17 and 18 of panel 1B.

The data in Table 2 show that the STAT complexes activated by GM-CSF, Epo, IL-3 and G-CSF can bind to a variety of DNA sequences of general structure TTN$_5$AA with varying affinities. In NFS-60 cells, G-CSF activated two STAT complexes that were distinguishable by their differing mobilities in an EMSA. The slower-migrating complex (Complex 1) comigrated with the STAT3 homodimer stimulated by IL-6 and was shown to contain STAT3 by antibody supershift experiments using a specific STAT3 antiserum (available from Upstate Biotechnology Incorporated, New York), and would selectively bind to a DNA sequence with a TTN$_4$AA structure (e.g., SEQ ID NO. 54). The faster-migrating complex (Complex 2) contained an unidentified STAT complex that migrated like the STAT complexes activated by IL-3 and GM-CSF. The two G-CSF-activated complexes had markedly different affinities for some of the regulatory elements (e.g. SEQID 54 vs SEQID 56).

Transient Transfection Assays

The reporter plasmids SEQID14×4-TK-LUC, SEQID16×4-TK-LUC, SEQID18×4-TK-LUC, SEQID20×4-TK-LUC, SEQID22×4-TK-LUC, SEQID24×4-TK-LUC, SEQID26×4-TK-LUC, SEQID28×4-TK-LUC, SEQID30×4-TK-LUC, SEQID32×4-TK-LUC, SEQID34×4-TK-LUC, SEQID36×4-TK-LUC, SEQID38×4-TK-LUC, SEQID40×4-TK-LUC, SEQID42×4-TK-LUC, SEQID44×4-TK-LUC, SEQID46×4-TK-LUC, SEQID48×4-TK-LUC, SEQID50×4-TK-LUC, SEQID52×4-TK-LUC, SEQID52×6-TK-LUC, SEQID54×4-TK-LUC, SEQID56×4-TK-LUC, and SEQID58×4-TK-LUC contain four copies (or six copies for SEQID52×6-TK-LUC) of the same SEQ ID NOs 14–58 as those used in the EMSA's, linked to the promoter of the Herpes Simplex virus thymidine kinase gene at position −35 with respect to the cap site. See FIG. 1A & 1B The reference reporter, TK-LUC (P. Lamb et al., 83 Blood 2063 (1994)), the disclosure of which is herein incorporated by reference, is the parent vector that contains no response element. These chimetic promoters drive the expression of the structural gene for firefly luciferase.

ME-180 cells were transfected with the reporter plasmids of above by calcium phosphate coprecipitation. Cells were seeded at 1–4×10$^5$/ml the day before transfection. Cells were exposed to a calcium phosphate precipitate containing the above reporter plasmids (10–20 µg/ml) and the β-galactosidase-expressing plasmid pCH 110 (5 µg/ml, commercially available from Pharmacia Biotech, Piscataway, N.J.) for 12 h. The medium was then changed and the cells allowed to recover for 16–18 h. Recombinant cytokines were then added prediluted in growth medium and the cells harvested after 6 h. Cells were lysed and luciferase and β-galactosidase activities determined using standard techniques. See, e.g. J. R. De Wet et al., 7 Mol. Cell. Biol. 725 (1987) and Sambrook et al., Molecular Cloning: A Laboratory Manual 2nd ed., Cold Spring Harbor Laboratory Press, Cold Spring Harbor, N.Y. (1989). For each sample the normalized response was determined by dividing light units obtained from the luciferase assay with the β-galactosidase activity in the same lysate as determined using a chromogenic substrate. The results of these transfections are shown below in Table 3. Numbers given are the mean fold inductions ('fold induction' is defined as the normalized response in a cytokine-treated sample divided by the normalized response in an untreated sample). The value in parentheses is the number of independent experiments included to calculate the mean.

TF-1 cells were transfected with the reporter plasmids of above by the DEAE-dextran method as described (J. Suzow and A. D. Friedman, 13 Mol. Cell. Biol. 2141 (1993)) with the following modifications: test reporter constructs were added to a concentration of 3 µg/mL during the transfection, pMSVCAT vector was not added to the transfection mixtures, the growth medium used was as described above for TF-1 cells, and cytokine inductions were carried out for 4–5 h. Cells were lysed and luciferase activity determined using standard techniques. Transfections were performed in a batch, and identical numbers of transfected cells were then separately induced with cytokine for the 4–5 h induction period. The results of these transfections are shown below in Table 4. Numbers given are the mean fold inductions ('fold induction' for TF-1 transfections is defined as the luciferase response in a cytokine-treated sample divided by the luciferase response in an untreated sample). The value in parentheses is the number of independent experiments included to calculate the mean.

NFS-60 cells were transfected with the reporter plasmids described above by the DEAE-dextran method as described in the preceding paragraph with the following modifications: test reporter constructs were added to a concentration of 6 µg/mL during the transfection, and cytokine inductions were carried out for 2.5 h. The results of these transfections are shown below in Table 5.

Stable Transfection of NFS-60 Cells

Stable transfection of NFS-60 cells was accomplished as described by H. Pahl et al., 19 *Exp. Hematol.*, 1038–1041 (1991). In brief, $1.4 \times 10^7$ factor-independent NFS-60 cells were washed twice with RPMI-1640 and then resuspended in RPMI-1640 (0.5 mL); linearized reporter DNA (16 μg) and EcoRI-digested pSV2NEO plasmid (4 μg, commercially available from ATCC) were then added. Cells and plasmids were incubated for 5 min at RT in a 0.4 cm electroporation cuvette (Bio-Rad), then subjected to a 330V, 960 μF pulse, using a Bio-Rad Gene Pulser. Cells were immediately incubated on ice for 15 min, then placed in normal growth medium (10 mL). Two days later, G418 (300 μg/mL, Boehringer-Mannheim, Indianapolis, Ind.) was added to the culture. Stably transfected cells were cloned by limiting dilution. Approximately 400 clones were screened for G-CSF-inducible luciferase activity, and 16 positive clones were identified and characterized further. The results for four of the positive clones are summarized in Table 6. The number of independent experiments included to calculate the mean is indicated in parentheses.

TABLE 3

Transcriptional induction in ME-180 cells of reporter constructs incorporating multiple copies of test STAT regulatory elements. The values given are mean fold inductions in response to the indicated cytokine. The value in the parentheses is the number of experiments included to calculate the mean.

| Reporter | Core Element | IL-4 | IL-13 |
| --- | --- | --- | --- |
| TK-LUC | none | 0.9 (3) | 1.0 (3) |
| SEQID14x4TK-LUC | CACTTCCCAAGAACAG | 22 (3) | 9.7 (3) |
| SEQID16x4TK-LUC | TGCTTCCCCGGAACGT | 1.3 (3) | 1.0 (3) |
| SEQID18x4TK-LUC | TGCTTCCCCAGAACGT | 1.2 (3) | 1.1 (3) |
| SEQID20x4TK-LUC | TGCTTCCCAAGAACGT | 1.5 (3) | 1.2 (3) |
| SEQID22x4TK-LUC | CACTTCCCCGGAACAG | 2.7 (3) | 1.6 (3) |
| SEQID24x4TK-LUC | CACTTCCCCAGAACAG | 8.0 (3) | 3.0 (3) |
| SEQID26x4TK-LUC | CACTTCCCAGGAACAG | 10 (3) | 6.4 (3) |
| SEQID28x4TK-LUC | TACTTCCCAAGAACAT | 3.0 (3) | 1.5 (3) |
| SEQID30x4TK-LUC | CGCTTCCCAAGAACGG | 1.5 (3) | 1.3 (3) |
| SEQID32x4TK-LUC | CACTTCTTAAGAACAG | 7.3 (3) | 3.3 (3) |
| SEQID34x4TK-LUC | CACTTTCCAAGAACAG | 1.2 (3) | 1.1 (3) |
| SEQID36x4TK-LUC | TGCTTCCCGGAACGT | 1.1 (3) | n.d. |
| SEQID38x4TK-LUC | GATTTCCCCGAAATG | 0.8 (3) | n.d. |
| SEQID40x4TK-LUC | ATATTCCTGTAAGTG | 1.2 (3) | n.d. |
| SEQID44x4TK-LUC | CATTTCTGGAAATG | 1.1 (3) | n.d. |
| SEQID46x4TK-LUC | CATTTCCCGTAAATC | 1.0 (3) | n.d. |
| SEQID48x4TK-LUC | ATATTACCAGAAATG | 1.2 (3) | n.d. |
| SEQID50x4TK-LUC | ATTTTCCAGTAACAG | 1.0 (3) | n.d. |
| SEQID52x4TK-LUC | CAATTTCTAAGAAAGGA | 0.8 (3) | n.d. |
| SEQID56x4TK-LUC | TGCTTCTCAGAACGT | 1.2 (3) | n.d. |
| SEQID58x4TK-LUC | TGCTTCCCCGAACGT | 1.2 (3) | n.d. | n.d. = not determined

TABLE 4

Transcriptional induction in TF-1 cells of reporter constructs incorporating multiple copies of test STAT regulatory elements. The values given are mean fold inductions in response to the indicated cytokine. The value in the parentheses is the number of experiments included to calculate the mean.

| Reporter | IL-4 | GM-CSF | Epo | IL-3 |
| --- | --- | --- | --- | --- |
| TK-LUC | 0.7 (2) | 0.8 (2) | 0.8 (2) | 0.7 (2) |
| SEQID36 × 4TK-LUC | n.d. | 3.4 (2) | 1.8 (2) | 2.8 (2) |
| SEQID38 × 4TK-LUC | 1.4 (2) | 9.6 (4) | 3.1 (4) | 6.8 (3) |
| SEQID40 × 4TK-LUC | n.d. | n.d. | 1.2 (2) | 1.3 (2) |
| SEQID42 × 4TK-LUC | n.d. | n.d. | 1.0 (2) | 1.2 (2) |
| SEQID44 × 4TK-LUC | n.d. | n.d. | 1.8 (3) | 0.9 (3) |

TABLE 4-continued

Transcriptional induction in TF-1 cells of reporter constructs incorporating multiple copies of test STAT regulatory elements. The values given are mean fold inductions in response to the indicated cytokine. The value in the parentheses is the number of experiments included to calculate the mean.

| Reporter | IL-4 | GM-CSF | Epo | IL-3 |
| --- | --- | --- | --- | --- |
| SEQID46 × 4TK-LUC | n.d. | n.d. | 0.8 (2) | 0.9 (2) |
| SEQID48 × 4TK-LUC | n.d. | n.d. | 1.2 (2) | 1.1 (2) |
| SEQID50 × 4TK-LUC | n.d. | n.d. | 1.5 (2) | 3.1 (2) |
| SEQID52 × 6TK-LUC | n.d. | 7.6 (2) | 3.5 (2) | 7.3 (2) |
| SEQID14 × 4TK-LUC | 3.3 (3) | 1.3 (2) | 0.8 (2) | 1.3 (2) | n.d. = not determined

TABLE 5

Transcriptional induction in NFS-60 cells of reporter constructs incorporating multiple copies of test STAT regulatory elements. The values given are mean fold inductions in response to the indicated cytokine. The value in the parentheses is the number of experiments included to calculate the mean.

| Reporter | Core Element | G-CSF | IL-3 | IL-6 |
| --- | --- | --- | --- | --- |
| SEQID54x4TK-LUC | TTCCCGAA | 14 (2) | 1.0 (2) | 4.1 (2) |
| SEQID36x4TK-LUC | TTCCCGGAA | 24 (2) | 3.5 (2) | 4.8 (2) |
| SEQID56x4TK-LUC | TTCTCAGAA | 3.1 (2) | 1.4 (2) | 1.7 (2) |
| SEQID38x4TK-LUC | TTCCCCGAA | 24 (2) | 6.1 (2) | 6.9 (2) |

TABLE 6

Transcriptional induction in NFS-60 cells stably transfected with the SEQID38 × 4TK-LUC reporter plasmid. The values given are mean fold inductions in response to the indicated cytokine. The value in the parentheses is the number of experiments included to calculate the mean.

| Clone Designation | G-CSF | IL-3 | IL-6 |
| --- | --- | --- | --- |
| 1E11 | 17.2 (3) | 16.5 (3) | 3.4 (3) |
| 6G8 | 17.3 (3) | 20.6 (3) | 3.6 (3) |
| 1B10 | 16.8 (3) | 27.6 (3) | 2.7 (3) |
| 4C2 | 12.8 (3) | 20.1 (3) | 2.3 (3) |

The data summarized in Table 3 when compared to the in vitro binding data described above clearly demonstrate that in vitro binding is not predictive of transcriptional activity. Thus, all of the DNA elements that were incorporated as multimers into the reporter vectors bound the STAT complexes activated by IL-4 and IL-13 with a similar affinity; however, surprisingly, not all could mediate transcriptional induction in response to IL-4 and IL-13 (defined as greater than a 2-fold induction). Although it has been reported that a sequence element found in the promoter of the FcεRIIb gene (SEQID52) is necessary for the IL-4 responsiveness of this gene and can bind the STAT complex activated by IL-4 in vitro (I. Köhler et al., 345 *FEBS Lett.* 187 (1994)), it is clear from the data in Table 3 (SEQID52×4TK-LUC entry) that this element is not sufficient on its own to mediate IL-4 responsiveness, further underscoring the disconnection between in vitro binding data and functional, transcriptional activity.

The data summarized in Table 4 when compared to the in vitro binding data described above again clearly demonstrate that in vitro binding cannot be relied on to be predictive of transcriptional activity. Thus, many of the DNA elements that were incorporated as multimers into the reporter vectors bound the STAT complexes activated by IL-4, GM-CSF, Epo and IL-3 with varying affinities (Table 2); however, most could not mediate a transcriptional induction in response to these cytokines (defined as greater than a 2-fold induction).

The data summarized in Table 5 again show that in vitro binding data do not reliably correlate with the ability of the elements to mediate a transcriptional induction. As described above, G-CSF activates two complexes in NFS-60 cells, one containing STAT3 and one containing an unidentified STAT protein resembling the complex activated by IL-3 in NFS-60 cells. Response elements that could bind to both G-CSF-activated complexes, such as SEQID38 and SEQID36, mediated a strong transcriptional induction in response to G-CSF, and the response element that bound strongly only to the STAT3-containing, G-CSF-activated complex (SEQID54) was activated by G-CSF (though not quite as strongly as were the sequences that bound both complexes). However, surprisingly, the response element that bound only the IL-3-activated complex (SEQID56) was not activated in response to IL-3 (defined as less than a 2-fold induction) and was only weakly activated by G-CSF.

The data summarized in Table 6 show that the NFS-60 clones stably transfected with SEQID38×4TK-LUC respond well to both G-CSF, IL-3 and IL-6 (though the response to IL-6 was slightly lower than what was obtained in the transient transfections). Also, compared to the transiently transfected NFS-60 cells, the stable NFS-60 clones appear to respond more robustly to IL-3. Nevertheless, in general, the transient transfection data are a good indicator of what to expect when the reporter is stably transfected into the NFS-60 cells.

It has previously been reported that many cytokines, including IL-3, GM-CSF, Epo, G-CSF, IL-4 and IL-13 activate STAT or STAT-like complexes that bind to DNA sequence elements related to the GAS element that was first characterized in the promoters of IFNγ-responsive genes. The data in Example 1 conclusively show that, surprisingly, in vitro binding is not predictive of transcriptional activation for the cytokines IL-3, IL-4, IL-13, GM-CSF, G-CSF and Epo. One can certainly not therefore assume that the in vitro STAT complex binding observed in previously published work is directly translatable into a functional reporter assay. To date there has been no reported demonstration that the DNA sequences reported to bind to the STAT or STAT-like complexes activated by IL-3, IL-4, IL-13, GM-CSF, G-CSF or Epo can mediate transcriptional induction in response to those cytokines. Because it is not possible to extrapolate from in vitro binding data that a given sequence will be functional, the demonstration of functional activity such as that shown in the example above is absolutely critical.

While in accordance with the patent statutes, description of the preferred weight fractions, and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

---

What is claimed is:

1. A method for measuring the ability of a compound to act as an agonist of cytokine-mediated gene transcription comprising:
   (a) contacting the compound with a cytokine-responsive host cell transfected with a DNA construct comprising:
      (i) an oligonucleotide sequence comprising a regulatory element of the nucleotide sequence TTN$_x$AA, operably linked to
      (ii) a promoter, operably linked to
      (iii) a heterologous gene, wherein N is independently selected from A, T, C or G and x is 4, 5, 6 or 7, and wherein the DNA construct is operably linked in such a manner that the heterologous gene is under the transcriptional control of the promoter and oligonucleotide sequence when the oligonucleotide sequence is trranscriptionally activated in response to IL-2, IL-3, IL-4, IL-7, IL-9, IL-13, IL-15, G-CSF, GM-CSF, Epo or Tpo under conditions in which expression of the heterologous gene is responsive to compounds which are agonists of cytokine-mediated gene transcription; and
   (b) comparing the level of gene expression in step (a) with the level of gene expression from the host cell in the absence of the compound, wherein the ability of the compound to act as an agonist of cytokine-mediated gene transcription is measured as the amount of increase in the level of gene expression in step (a) compared to the level of gene expression from the host cell in the absence of the compound.

2. A method for measuring the ability of a compound to act as an antagonist of cytokine-mediated gene transcription comprising:
   (a) contacting the compound with a cytokine-responsive host cell transfected with a DNA construct comprising:
      (i) an oligonucleotide sequence comprising a regulatory element of the nucleotide sequence TTN$_x$AA, operably linked to
      (ii) a promoter, operably linked to
      (iii) a heterologous gene, wherein N is independently selected from A, T, C or G and x is 4, 5, 6 or 7, and wherein the DNA construct is operably linked in such a manner that the heterologous gene is under the transcriptional control of the promoter and oligonucleotide sequence when the oligonucleotide sequence is transcriptionally activated in response to IL-2, IL-3, IL-4, IL-7, IL-9, IL-13, IL-15, G-CSF, GM-CSF, Epo or Tpo in the presence of a predetermined amount of a cytokine under conditions in which expression of the heterologous gene is responsive to the cytokine; and
   (b) comparing the level of gene expression in step (a) with the level of gene expression from the host cell in the presence of the cytokine, but the absence of the compound, wherein the ability of the compound to act as an antagonist of cytokine-mediated gene transcription is measured as the amount of decrease in the level of gene expression in step (a) compared to the level of gene expression from the host cell in the absence of the compound.

3. A method for measuring the ability of a compound to act as an agonist of cytokine-mediated gene transcription comprising:
   (a) contacting the compound with a cytokine-responsive host cell transfected with a DNA construct comprising:
      (i) an oligonucleotide sequence comprising a regulatory element of the nucleotide sequence ANTTCNNNNGAANA (SEQ ID NO. 3), or its double stranded complement, operably linked to
      (ii) a promoter, operably linked to
      (iii) a heterologous gene, wherein N is independently selected from A,T, C or G, and wherein the DNA construct is operably linked in such a manner that the heterologous gene is under the transcriptional control of the promoter and oligonucleotide sequence when the oligonucleotide sequence is transcriptionally activated in response to a STAT6-activating cytokine under conditions in which expression of the heterologous gene is responsive to compounds which are agonists of cytokine-mediated gene transcription; and
   (b) comparing the level of gene expression in step (a) with the level of gene expression from the host cell in the absence of the compound, wherein the ability of the compound to act as an agonist of cytokine-mediated gene transcription is measured as the amount of increase in the level of gene expression in step (a) compared to the level of gene expression from the host cell in the absence of the compound.

4. A method for measuring the ability of a compound to act as an antagonist of cytokine-mediated gene transcription comprising:
   (a) contacting the compound with a cytokine-responsive host cell transfected with a DNA construct comprising:
      (i) an oligonucleotide sequence comprising a regulatory element of the nucleotide sequence ANTTCNNNNGAANA (SEQ ID NO. 3), or its double stranded complement, operably linked to
      (ii) a promoter, operably linked to
      (iii) a heterologous gene, wherein N is independently selected from A, T, C or G, and wherein the DNA construct is operably linked in such a manner that the heterologous gene is under the transcriptional control of the promoter and oligonucleotide sequence when the oligonucleotide sequence is transcriptionally activated in response to a STAT6-activating cytokine in the presence of a predetermined amount of a cytokine under conditions in which expression of the heterologous gene is responsive to the cytokine; and (b) comparing the level of gene expression in step (a) with the level of gene expression from the host cell in the presence of the cytokine, but the absence of the compound, wherein the ability of the compound to act as an antagonist of cytokine-mediated gene transcription is measured as the amount of decrease in the level of gene expression in step (a) compared to the level of gene expression from the host cell in the absence of the compound.

* * * * *

SEQUENCE LISTING ( 1 ) GENERAL INFORMATION:

( i i i ) NUMBER OF SEQUENCES: 59

( 2 ) INFORMATION FOR SEQ ID NO:1:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:1:

TTCNNNGAA    9

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:2:

TTCNNNNGAA    10

( 2 ) INFORMATION FOR SEQ ID NO:3:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
              SYNTHETIC DNA"

( x i ) SEQUENCE DESCRIPTION: SEQ ID NO:3:

ANTTCNNNNG AANA 14

( 2 ) INFORMATION FOR SEQ ID NO:4:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
              SYNTHETIC DNA"

( x i ) SEQUENCE DESCRIPTION: SEQ ID NO:4:

ACTTCCCAAG AACA 14

( 2 ) INFORMATION FOR SEQ ID NO:5:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
              SYNTHETIC DNA"

( x i ) SEQUENCE DESCRIPTION: SEQ ID NO:5:

ACTTCCCCGG AACA 14

( 2 ) INFORMATION FOR SEQ ID NO:6:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
              SYNTHETIC DNA"

( x i ) SEQUENCE DESCRIPTION: SEQ ID NO:6:

ACTTCCCCAG AACA 14

( 2 ) INFORMATION FOR SEQ ID NO:7:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
              SYNTHETIC DNA"

( x i ) SEQUENCE DESCRIPTION: SEQ ID NO:7:

ACTTCCCAGG AACA    14

( 2 ) INFORMATION FOR SEQ ID NO:8:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:8:

ACTTCCTAAG AACA    14

( 2 ) INFORMATION FOR SEQ ID NO:9:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:9:

ACTTCTTAAG AACA    14

( 2 ) INFORMATION FOR SEQ ID NO:10:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:10:

TTCCCGGAA    9

( 2 ) INFORMATION FOR SEQ ID NO:11:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:11:

TTCCCCGAA    9

( 2 ) INFORMATION FOR SEQ ID NO:12:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear (ii) MOLECULE TYPE: other nucleic acid
    (A) DESCRIPTION: /desc = "OTHER NUCLEIC ACID, SYNTHETIC DNA"

(xi) SEQUENCE DESCRIPTION: SEQ ID NO:12:

TTCTAAGAA                                                                                                  9

(2) INFORMATION FOR SEQ ID NO:13:

(i) SEQUENCE CHARACTERISTICS:
       (A) LENGTH: 9 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "OTHER NUCLEIC ACID, SYNTHETIC DNA"

(xi) SEQUENCE DESCRIPTION: SEQ ID NO:13:

TTCTCAGAA                                                                                                  9

(2) INFORMATION FOR SEQ ID NO:14:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "OTHER NUCLEIC ACID, SYNTHETIC DNA"

(xi) SEQUENCE DESCRIPTION: SEQ ID NO:14:

GATCCACTTC CCAAGAACAG A                                                                                   21

(2) INFORMATION FOR SEQ ID NO:15:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "OTHER NUCLEIC ACID, SYNTHETIC DNA"

(xi) SEQUENCE DESCRIPTION: SEQ ID NO:15:

GATCTCTGTT CTTGGAAGT G                                                                                    21

(2) INFORMATION FOR SEQ ID NO:16:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "OTHER NUCLEIC ACID, SYNTHETIC DNA"

(xi) SEQUENCE DESCRIPTION: SEQ ID NO:16:

GATCTGCTTC CCCGGAACGT                                                                                     20

(2) INFORMATION FOR SEQ ID NO:17:

(i) SEQUENCE CHARACTERISTICS:

(A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "OTHER NUCLEIC ACID,
                SYNTHETIC DNA"

(xi) SEQUENCE DESCRIPTION: SEQ ID NO:17:

GATCACGTTC CGGGGAAGCA										20

(2) INFORMATION FOR SEQ ID NO:18:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "OTHER NUCLEIC ACID,
                SYNTHETIC DNA"

(xi) SEQUENCE DESCRIPTION: SEQ ID NO:18:

GATCTGCTTC CCCAGAACGT										20

(2) INFORMATION FOR SEQ ID NO:19:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "OTHER NUCLEIC ACID,
                SYNTHETIC DNA"

(xi) SEQUENCE DESCRIPTION: SEQ ID NO:19:

GATCACGTTC TGGGGAAGCA										20

(2) INFORMATION FOR SEQ ID NO:20:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "OTHER NUCLEIC ACID,
                SYNTHETIC DNA"

(xi) SEQUENCE DESCRIPTION: SEQ ID NO:20:

GATCTGCTTC CCAAGAACGT										20

(2) INFORMATION FOR SEQ ID NO:21:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "OTHER NUCLEIC ACID,
                SYNTHETIC DNA"

(xi) SEQUENCE DESCRIPTION: SEQ ID NO:21:

GATCACGTTC TTGGGAAGCA										20

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:22:

GATCCACTTC CCCGGAACAG A     21

( 2 ) INFORMATION FOR SEQ ID NO:23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:23:

GATCTCTGTT CCGGGGAAGT G     21

( 2 ) INFORMATION FOR SEQ ID NO:24:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:24:

GATCCACTTC CCCAGAACAG A     21

( 2 ) INFORMATION FOR SEQ ID NO:25:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:25:

GATCTCTGTT CTGGGGAAGT G     21

( 2 ) INFORMATION FOR SEQ ID NO:26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,

SYNTHETIC DNA"

( x i ) SEQUENCE DESCRIPTION: SEQ ID NO:26:

GATCCACTTC CCAGGAACAG A                                     21

( 2 ) INFORMATION FOR SEQ ID NO:27:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:27:

GATCTCTGTT CCTGGGAAGT G                                     21

( 2 ) INFORMATION FOR SEQ ID NO:28:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:28:

GATCTACTTC CCAAGAACAT A                                     21

( 2 ) INFORMATION FOR SEQ ID NO:29:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:29:

GATCTATGTT CTTGGGAAGT A                                     21

( 2 ) INFORMATION FOR SEQ ID NO:30:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:30:

GATCCGCTTC CCAAGAACGG A                                     21

( 2 ) INFORMATION FOR SEQ ID NO:31:

( i ) SEQUENCE CHARACTERISTICS:
        ( A ) LENGTH: 21 base pairs
        ( B ) TYPE: nucleic acid (C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:31:

GATCTCCGTT CTTGGGAAGC G  21

(2) INFORMATION FOR SEQ ID NO:32:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:32:

GATCCACTTC TTAAGAACAG A  21

(2) INFORMATION FOR SEQ ID NO:33:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:33:

GATCTCTGTT CTTAAGAAGT G  21

(2) INFORMATION FOR SEQ ID NO:34:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:34:

GATCCACTTT CCAAGAACAG A  21

(2) INFORMATION FOR SEQ ID NO:35:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:35:

GATCTCTGTT CTTGGAAAGT G  21

( 2 ) INFORMATION FOR SEQ ID NO:36:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:36:

GATCTGCTTC CCGGAACGT            19

( 2 ) INFORMATION FOR SEQ ID NO:37:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:37:

GATCACGTTC CGGGAAGCA            19

( 2 ) INFORMATION FOR SEQ ID NO:38:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:38:

GATCGATTTC CCCGAAATG            19

( 2 ) INFORMATION FOR SEQ ID NO:39:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:39:

GATCCATTTC GGGGAAATC            19

( 2 ) INFORMATION FOR SEQ ID NO:40:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:40:

GATCATATTC CTGTAAGTG    19

( 2 ) INFORMATION FOR SEQ ID NO:41:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:41:

GATCCACTTA CAGGAATAT    19

( 2 ) INFORMATION FOR SEQ ID NO:42:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:42:

GATCATATTC CCGTAAGTG    19

( 2 ) INFORMATION FOR SEQ ID NO:43:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:43:

GATCCACTTA CGGGAATAT    19

( 2 ) INFORMATION FOR SEQ ID NO:44:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:44:

GATCCATTTC TGGAAATG    18

( 2 ) INFORMATION FOR SEQ ID NO:45:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:45:

GATCCATTTC CAGAAATG                                     18

( 2 ) INFORMATION FOR SEQ ID NO:46:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:46:

GATCCATTTC CCGTAAATC                                    19

( 2 ) INFORMATION FOR SEQ ID NO:47:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:47:

CTAGGATTTA CGGGAAATG                                    19

( 2 ) INFORMATION FOR SEQ ID NO:48:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:48:

GATCATATTA CCAGAAATG                                    19

( 2 ) INFORMATION FOR SEQ ID NO:49:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:49:

GATCCATTTC TGGTAATAT                                    19

( 2 ) INFORMATION FOR SEQ ID NO:50:

( i ) SEQUENCE CHARACTERISTICS:
   ( A ) LENGTH: 19 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "OTHER NUCLEIC ACID, SYNTHETIC DNA"

( x i ) SEQUENCE DESCRIPTION: SEQ ID NO:50:

GATCATTTTC CAGTAACAG 19

( 2 ) INFORMATION FOR SEQ ID NO:51:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "OTHER NUCLEIC ACID, SYNTHETIC DNA"

( x i ) SEQUENCE DESCRIPTION: SEQ ID NO:51:

GATCCTGTTA CTGGAAAAT 19

( 2 ) INFORMATION FOR SEQ ID NO:52:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "OTHER NUCLEIC ACID, SYNTHETIC DNA"

( x i ) SEQUENCE DESCRIPTION: SEQ ID NO:52:

GATCCAATTT CTAAGAAAGG A 21

( 2 ) INFORMATION FOR SEQ ID NO:53:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "OTHER NUCLEIC ACID, SYNTHETIC DNA"

( x i ) SEQUENCE DESCRIPTION: SEQ ID NO:53:

GATCTCCTTT CTTAGAAATT G 21

( 2 ) INFORMATION FOR SEQ ID NO:54:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "OTHER NUCLEIC ACID, SYNTHETIC DNA"

( x i ) SEQUENCE DESCRIPTION: SEQ ID NO:54:

```
GATCTGCTTC CCGAACGT                                                                                    18
```

(2) INFORMATION FOR SEQ ID NO:55:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:55:

```
GATCACGTTC GGGAAGCA                                                                                    18
```

(2) INFORMATION FOR SEQ ID NO:56:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:56:

```
GATCTGCTTC TCAGAACGT                                                                                   19
```

(2) INFORMATION FOR SEQ ID NO:57:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:57:

```
GATCACGTTC TGAGAAGCA                                                                                   19
```

(2) INFORMATION FOR SEQ ID NO:58:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:58:

```
GATCTGCTTC CCCGAACGT                                                                                   19
```

(2) INFORMATION FOR SEQ ID NO:59:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid ( A ) DESCRIPTION: /desc = "OTHER NUCLEIC ACID, SYNTHETIC DNA"

( x i ) SEQUENCE DESCRIPTION: SEQ ID NO:59:

GATCACGTTC GGGGAAGCA 19